(12) United States Patent
Yoo et al.

(10) Patent No.: US 11,329,235 B1
(45) Date of Patent: May 10, 2022

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Jae Duk Yoo, Cheonan-si (KR); Jong Gwang Park, Cheonan-si (KR); Soung Yun Mun, Cheonan-si (KR); Yun Suk Lee, Cheonan-si (KR); In Goo Lee, Cheonan-si (KR); Guang Ming Li, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 17/454,599

(22) Filed: Nov. 11, 2021

(30) Foreign Application Priority Data

Aug. 5, 2021 (KR) .......................... 10-2021-0103124

(51) Int. Cl.
*C07D 487/04* (2006.01)
*H01L 51/00* (2006.01)
*H01L 51/50* (2006.01)

(52) U.S. Cl.
CPC ........ *H01L 51/0072* (2013.01); *C07D 487/04* (2013.01); *H01L 51/0061* (2013.01); *H01L 51/0074* (2013.01); *H01L 51/5016* (2013.01)

(58) Field of Classification Search
CPC .......................... C07D 487/04; H01L 51/0072
See application file for complete search history.

(56) References Cited

FOREIGN PATENT DOCUMENTS

| KR | 10-2017-0075877 A | 7/2017 | |
|---|---|---|---|
| KR | 10-2019-0034074 A | 4/2019 | |
| KR | 20190034074 A * | 4/2019 | ........... C09K 11/025 |
| KR | 10-2020-0026083 A | 3/2020 | |
| KR | 10-2021-0003041 A | 1/2021 | |
| KR | 10-2021-0039315 A | 4/2021 | |

OTHER PUBLICATIONS

Notice of Allowance, dated Sep. 2, 2021, for corresponding Korean application No. 10-2021-0103124, five pages.

* cited by examiner

*Primary Examiner* — Vu A Nguyen
(74) *Attorney, Agent, or Firm* — Vorys, Sater, Seymour and Pease LLP; Mih Suhn Koh

(57) ABSTRACT

Provided are a novel compound capable of improving the luminous efficiency, stability and lifespan of an element, an organic electronic element using the same, and an electronic device thereof.

17 Claims, 4 Drawing Sheets

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and according to the light emission mechanism, it can be classified into a fluorescent material derived from a singlet excited state of an electron and a phosphorescent material derived from a triplet excited state of an electron. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. At this time, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

In other words, in order to fully exhibit the excellent characteristics of an organic electronic element, the material constituting the organic material layer in the device, such as a hole injection material, a hole transport material, a light emitting material, an electron transport material, an electron injection material, etc., should be a stable and efficient material, but the development of a stable and efficient material for the organic layers for an organic electronic device has not yet been sufficiently made. Therefore, the development of new materials is continuously required, and in particular, the development of a host material for the emitting layer is urgently required.

DETAILED DESCRIPTION OF THE INVENTION

Summary

In order to solve the problems of the above-mentioned background art, the present invention has revealed a compound having a novel structure, and when this compound is applied to an organic electronic element, it has been found that the driving voltage, efficiency and lifespan of the device can be significantly improved.

Accordingly, an object of the present invention is to provide a novel compound, an organic electronic element using the same, and an electronic device thereof.

Technical Solution

The present invention provides a compound represented by Formula (1).

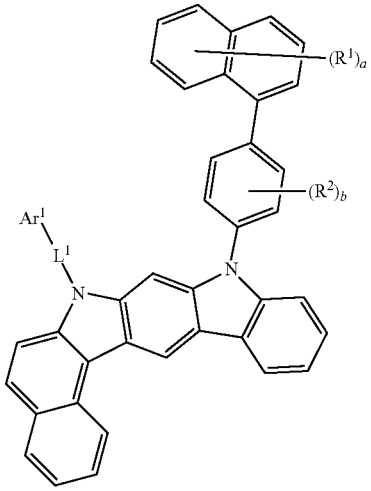

Formula (1)

In another aspect, the present invention provides an organic electronic element comprising the compound represented by Formula 1 and an electronic device thereof.

Effects of the Invention

By using the compound according to the present invention, high luminous efficiency, low driving voltage and high heat resistance of the device can be achieved, and color purity and lifespan of the device can be greatly improved.

| | | | |
|---|---|---|---|
| 100, 200, 300: | organic electronic element | 110: | the first electrode |
| 120: | hole injection layer | 130: | hole transport layer |
| 140: | emitting layer | 150: | electron transport layer |
| 160: | electron injection layer | 170: | second electrode |
| 180: | light efficiency enhancing Layer | 210: | buffer layer |
| 220: | emitting-auxiliary layer | 320: | first hole injection layer |
| 330: | first hole transport layer | 340: | first emitting layer |
| 350: | first electron transport layer | 360: | first charge generation layer |
| 361: | second charge generation layer | 420: | second hole injection layer |
| 430: | second hole transport layer | 440: | second emitting layer |
| 450: | second electron transport layer | CGL: | charge generation layer |
| ST1: | first stack | ST2 : | second stack |

Figure 4:
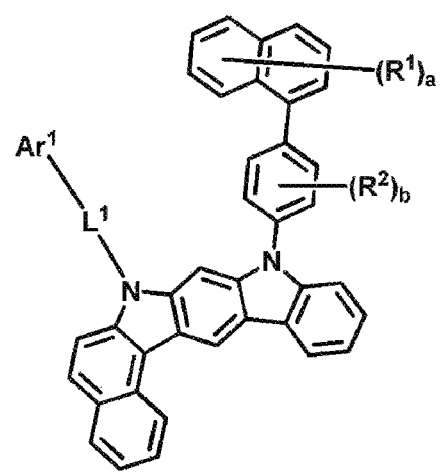

FIG. 4 illustrates a formula according to an aspect of the present invention.

DETAILED DESCRIPTION OF THE INVENTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled", or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

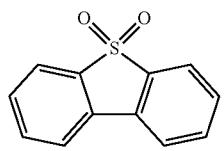 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

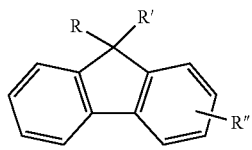

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

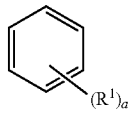

Here, when a is an integer of zero, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

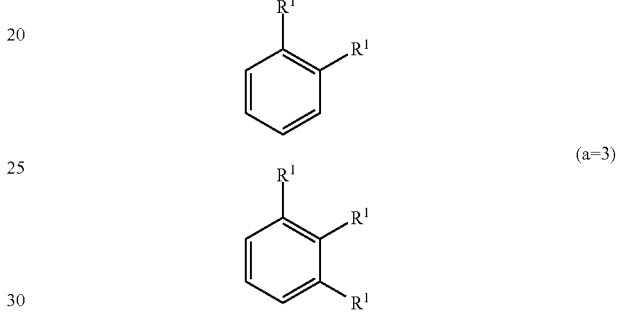

Hereinafter, a compound according to an aspect of the present invention and an organic electronic element including the same will be described.

The present invention provides a compound represented by Formula 1.

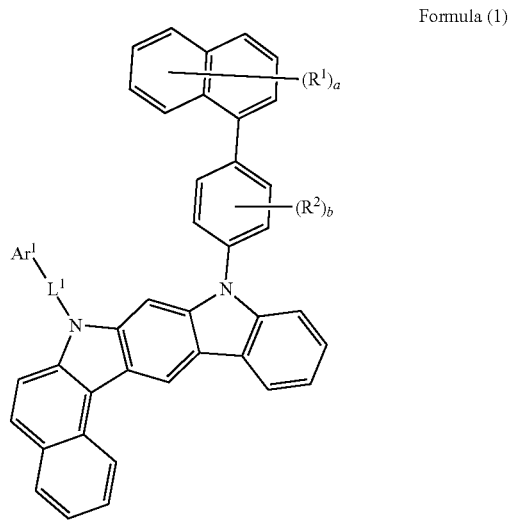

Formula (1)

Wherein, each symbol may be defined as follows.

1) $Ar^1$ is selected from the group consisting of a $C_6$-$C_{60}$ aryl group; a fluorenyl group; a $C_2$-$C_{60}$ heterocyclic group including at least one heteroatom of O, N, S, Si or P; $L'$-$NR^aR^b$;

When $Ar^1$ may be an aryl group, it may be preferably a $C_6$-$C_{30}$ aryl group, more preferably a $C_6$-$C_{25}$ aryl group, such as phenylene, biphenyl, naphthalene, terphenyl, etc.;

When $Ar^1$ is a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

2) $L^1$ and $L'$ are each independently selected from the group consisting of a single bond; a $C_6$-$C_{60}$ arylene group; and a $C_2$-$C_{60}$ heterocyclic group including at least one heteroatom of O, N, S, Si or P;

When $L^1$ and $L'$ are an arylene group, it may be preferably a $C_6$-$C_{30}$ arylene group, more preferably a $C_6$-$C_{24}$ arylene group, for example, phenylene, biphenyl, naphthalene, terphenyl, etc.

When $L^1$ and $L'$ are a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

3) $R^a$ and $R^b$ are each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P; an $C_1$~$C_{50}$ alkyl group, an $C_2$~$C_{20}$ alkenyl group, a $C_2$-$C_{20}$ alkynyl group, a $C_1$-$C_{30}$ alkoxy group, and a $C_6$-$C_{30}$ aryloxy group, When $R^a$ and $R^b$ are an aryl group, it may be preferably a $C_6$-$C_{30}$ aryl group, and more preferably a $C_6$-$C_{25}$ aryl group, for example, phenylene, biphenyl, naphthyl, terphenyl, etc.

When $R^a$ and $R^b$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^a$ and $R^b$ are a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

When $R^a$ and $R^b$ are an alkyl group, it may be preferably a $C_1$-$C_{30}$ alkyl group, and more preferably a $C_1$-$C_{24}$ alkyl group.

When $R^a$ and $R^b$ are an alkoxy group, it may preferably be $C_1$-$C_{24}$ alkoxy groups.

When $R^a$ and $R^b$ are an aryloxy group, it may preferably be $C_6$-$C_{24}$ aryloxy groups.

4) $R^1$ and $R^2$ are deuterium, 5) a is an integer from 0 to 7, b is an integer from 0 to 4, 6) wherein, the aryl group, arylene group, heterocyclic group, fluorenyl group, fused ring group, alkyl group, alkenyl group, alkynyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; $C_8$-$C_{20}$ arylalkenyl group; and -L'-$NR^aR^b$; or the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, the present invention provides a compound in which Formula (1) is represented by Formula (1-1).

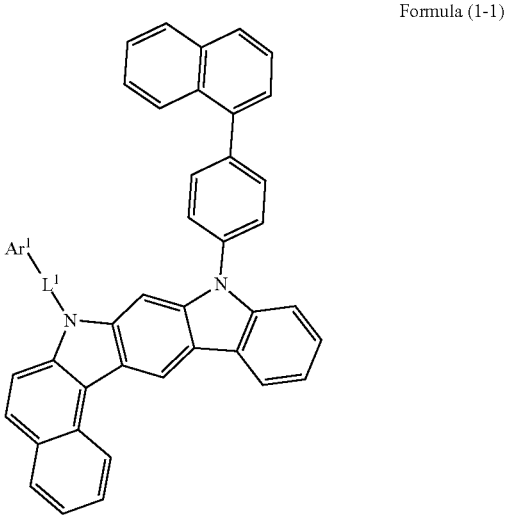

Formula (1-1)

{Wherein $Ar^1$ and $L^1$ are as defined in Formula (1)}

Also, the present invention provides a compound in which the Formula (1) is represented by the Formula (1-2).

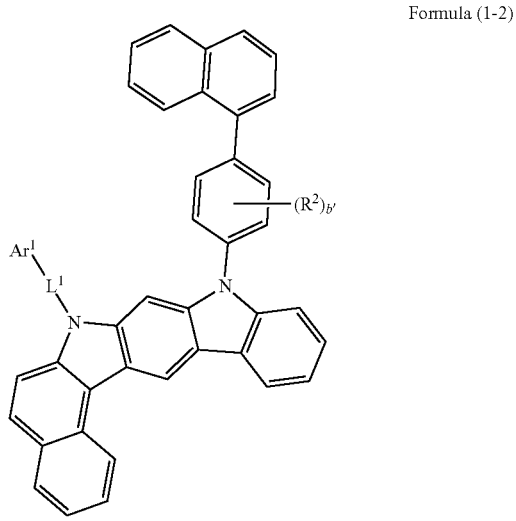

Formula (1-2)

{Wherein

1) $Ar^1$ and $L^1$ and $R^2$ are the same as defined in Formula (1), 2) b' is an integer from 1 to 4.}

Also, the present invention provides a compound in which the Formula (1) is represented by the Formula (1-3).

Formula (1-3)

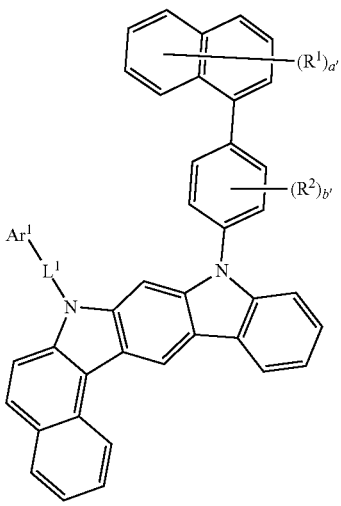

{Wherein
1) $Ar^1$, $L^1$, $R^1$ and $R^2$ are the same as defined in Formula (1),
2) a' is an integer from 1 to 7, and b' is an integer from 1 to 4.}

Also, $L^1$ is a single bond; or a $C_6$-$C_{60}$ arylene group; $Ar^1$ is a $C_6$-$C_{18}$ aryl group.

Also, the present invention provides a compound in which the Formula (1) is represented by the Formula (2-1).

Formula (2-1)

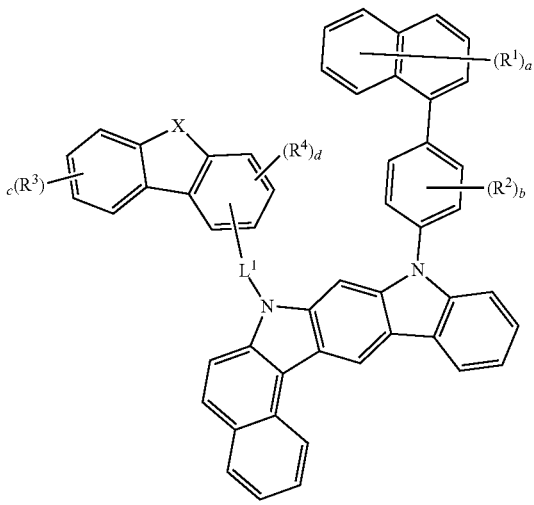

wherein, each symbol may be defined as follows.
1) X is O, S or $NR^c$,
2) $R^3$ and $R^4$ are each independently selected from the group consisting of hydrogen; a $C_6$-$C_{60}$ aryl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; an $C_1$~$C_{50}$ alkyl group, an $C_2$~$C_{20}$ alkenyl group, a $C_2$-$C_{20}$ alkynyl group, a $C_1$-$C_{30}$ alkoxy group, and a $C_6$-$C_{30}$ aryloxy group, and -L'-$NR^aR^b$; or a plurality of adjacent $R^3$ or a plurality of $R^4$ may be bonded to each other to form a ring, When $R^3$ and $R^4$ are an aryl group, it may be preferably a $C_6$-$C_{30}$ aryl group, and more preferably a $C_6$-$C_{25}$ aryl group, for example, phenylene, biphenyl, naphthyl, terphenyl, etc.

When $R^3$ and $R^4$ are a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

When $R^3$ and $R^4$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^3$ and $R^4$ are an alkyl group, it may be preferably a $C_1$-$C_{30}$ alkyl group, and more preferably a $C_1$-$C_{24}$ alkyl group.

When $R^3$ and $R^4$ are an alkoxy group, it may preferably be $C_1$-$C_{24}$ alkoxy groups.

When $R^3$ and $R^4$ are an aryloxy group, it may preferably be $C_6$-$C_{24}$ aryloxy groups.

3) c is an integer of 0 to 4, d is an integer of 0 to 3,
4) $L^1$, $R^1$, $R^2$, a, b, L', $R^a$ and $R^b$ are the same as defined in Formula (1),
5) $R^c$ is each independently selected from the group consisting of a hydrogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; an $C_1$-$C_{60}$ alkyl group, an $C_2$~$C_{20}$ alkenyl group, a $C_2$-$C_{20}$ alkynyl group, a $C_1$-$C_{30}$ alkoxy group, and a $C_6$-$C_{30}$ aryloxy group, When $R^c$ is an aryl group, it may be preferably a $C_6$-$C_{30}$ aryl group, and more preferably a $C_6$-$C_{25}$ aryl group, for example, phenylene, biphenyl, naphthyl, terphenyl, etc.

When $R^c$ is an a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

When $R^c$ is an a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^c$ is an alkyl group, it may be preferably a $C_1$-$C_{30}$ alkyl group, and more preferably a $C_1$-$C_{24}$ alkyl group.

When $R^c$ is an alkoxy group, it may preferably be $C_1$-$C_{24}$ alkoxy groups.

When $R^c$ is an aryloxy group, it may preferably be $C_6$-$C_{24}$ aryloxy groups.

Also, the present invention provides a compound having a $\Delta E_{st}$ value of 0.2100 or less of the compound represented by Formula (1).

Also, the present invention provides a compound having a $\Delta E_{st}$ value of 0.150 to 0.2100 of the compound represented by Formula (1).

Also, the compound represented by Formula (1) is represented by any of the following compounds P-1 to P-60

P-1
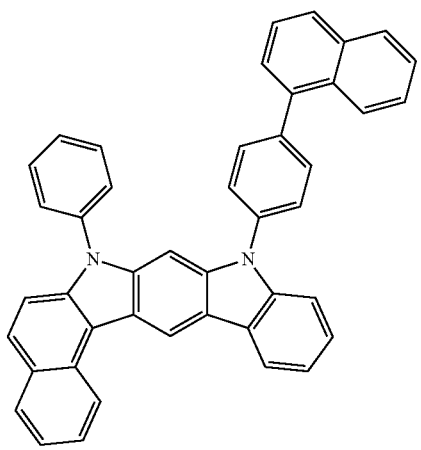
P-2
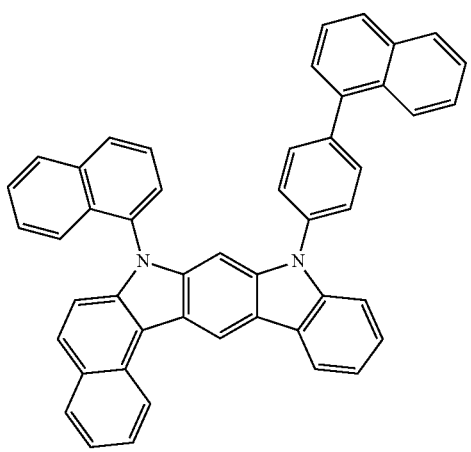
P-3
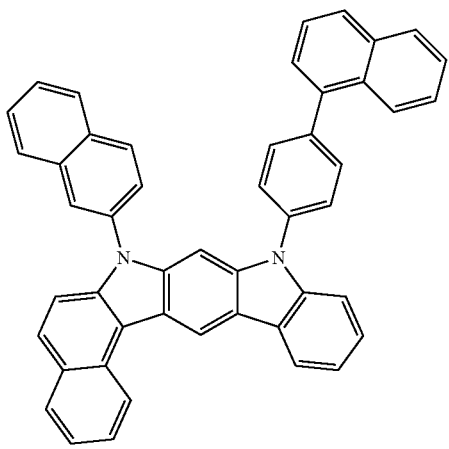
P-4
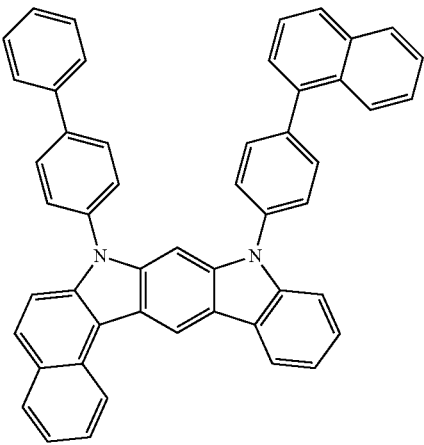
P-5
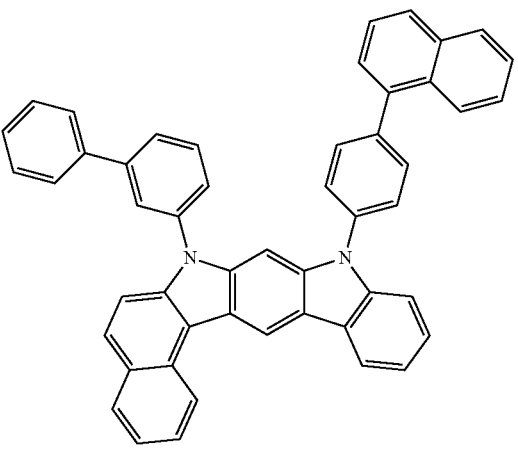
P-6
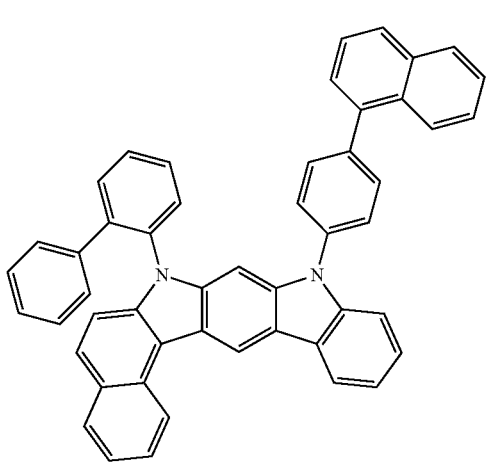

P-7
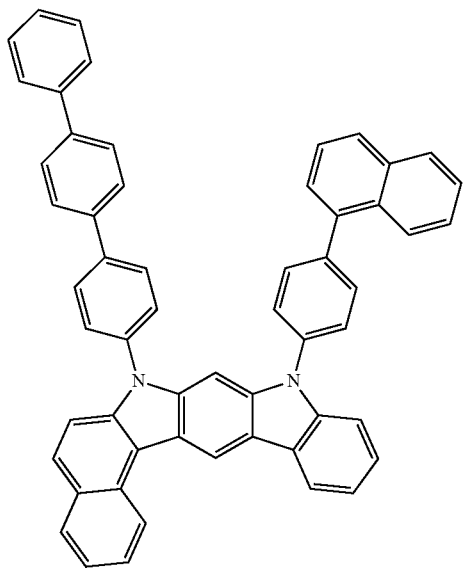
P-8
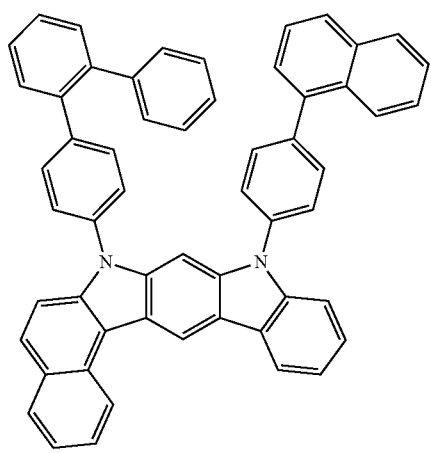
P-9
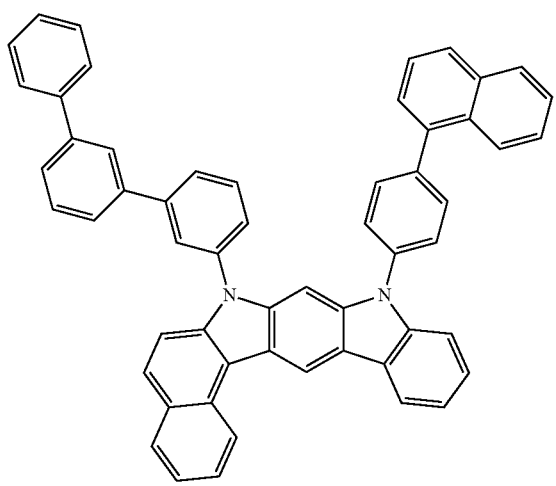
P-10
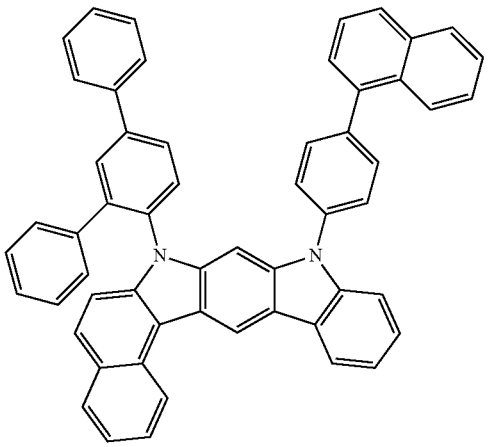
P-11
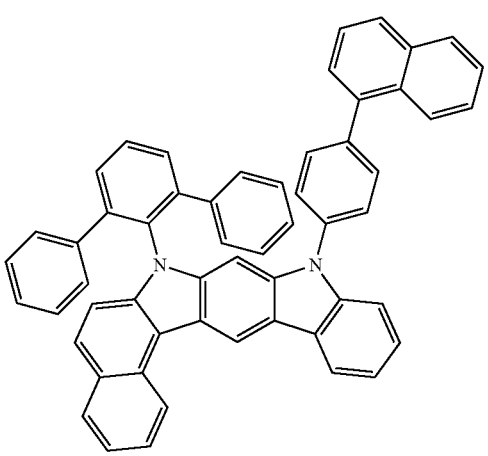
P-12
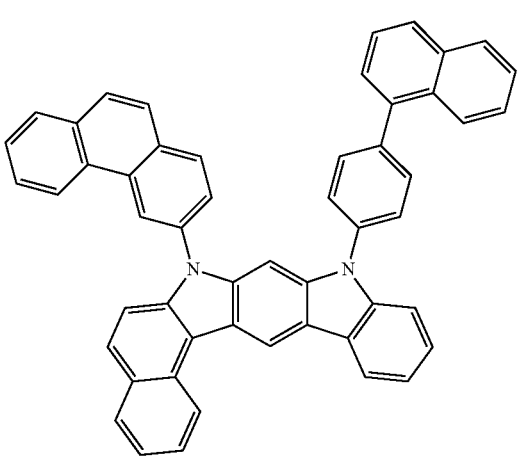

P-13
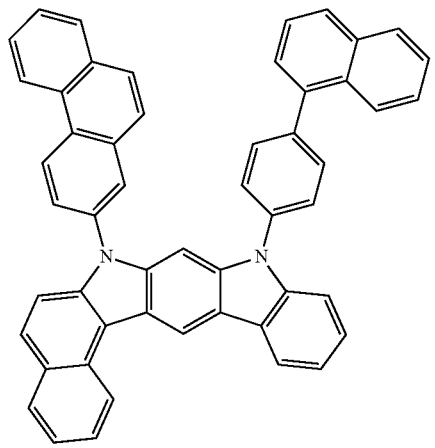
P-16
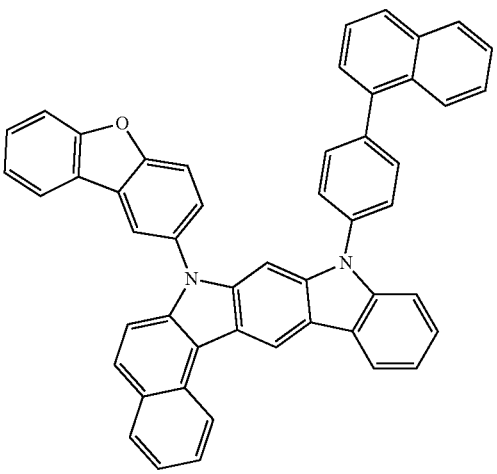
P-14
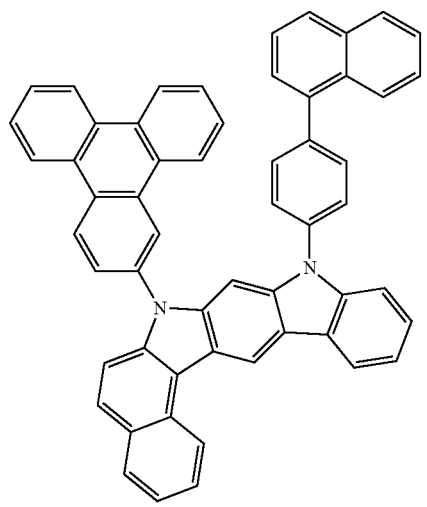
P-17
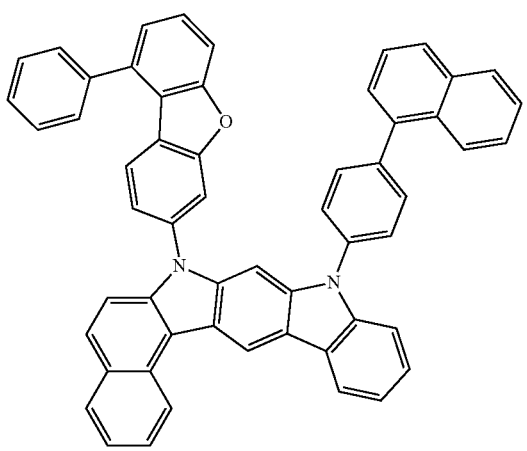
P-15
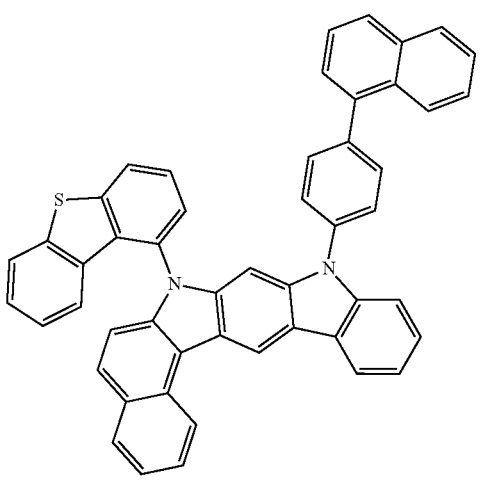
P-18
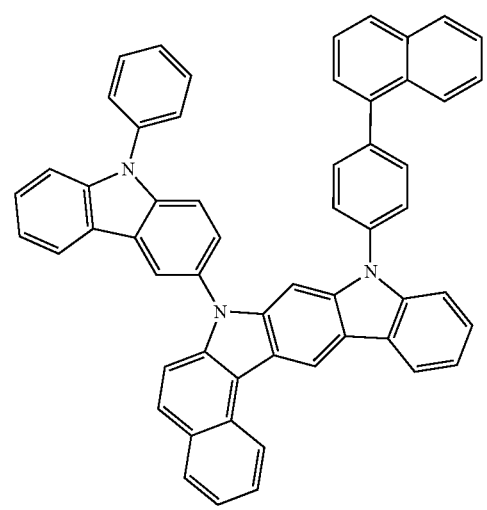

P-19
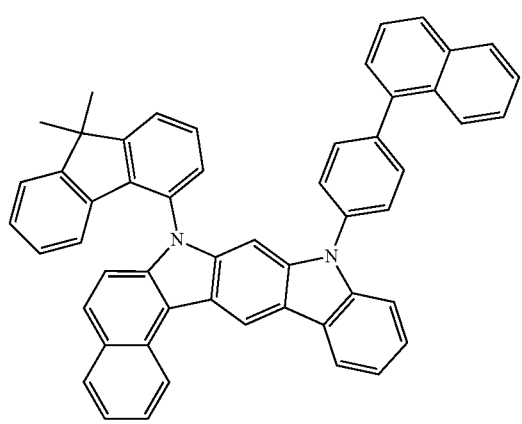
P-22
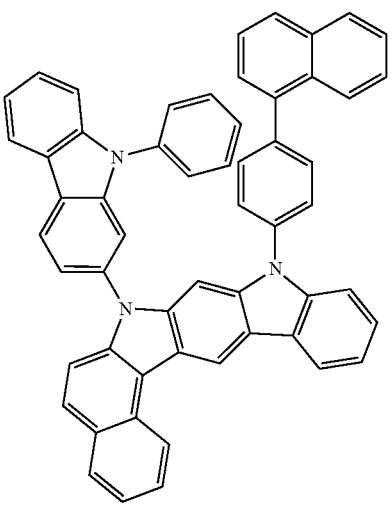
P-20
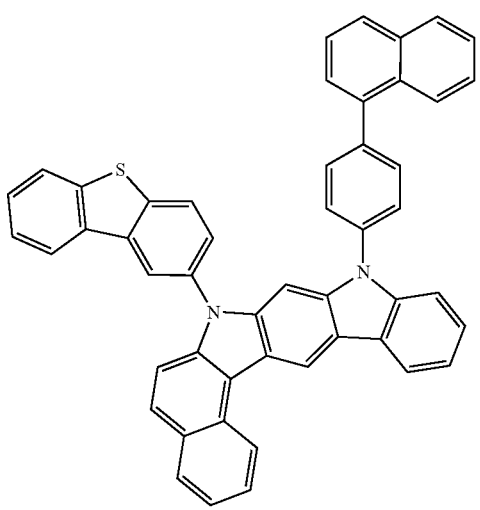
P-23
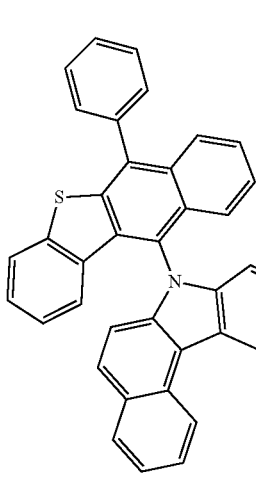
P-21
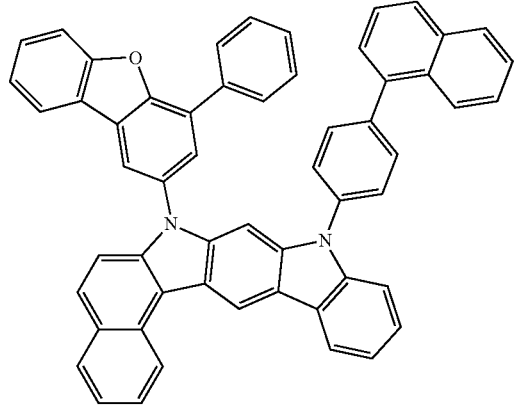
P-24
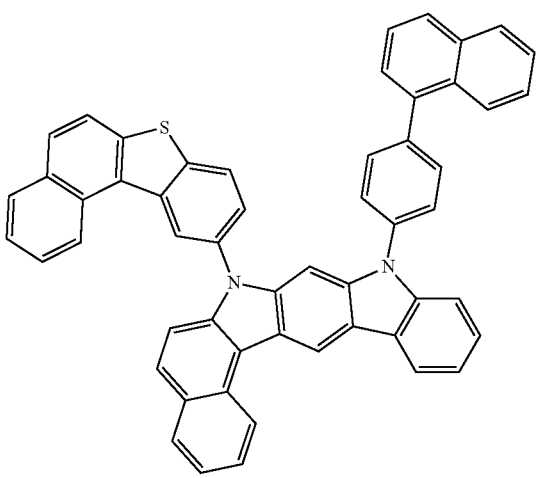

P-25
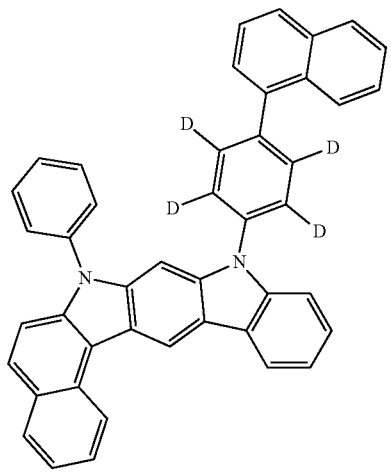
P-26
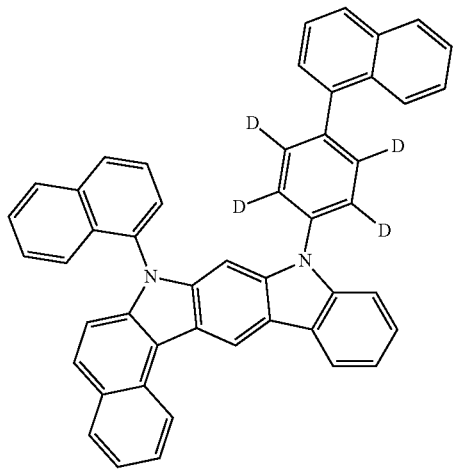
P-27
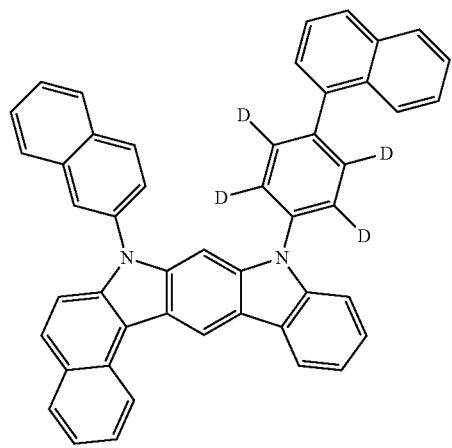
P-28
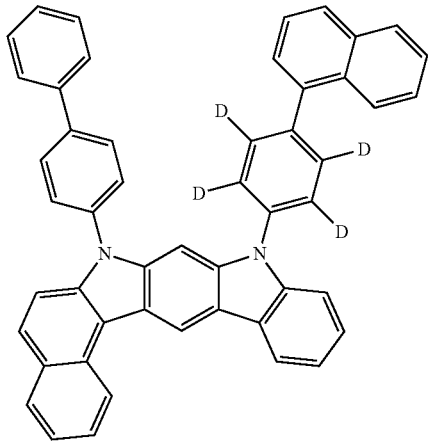
P-29
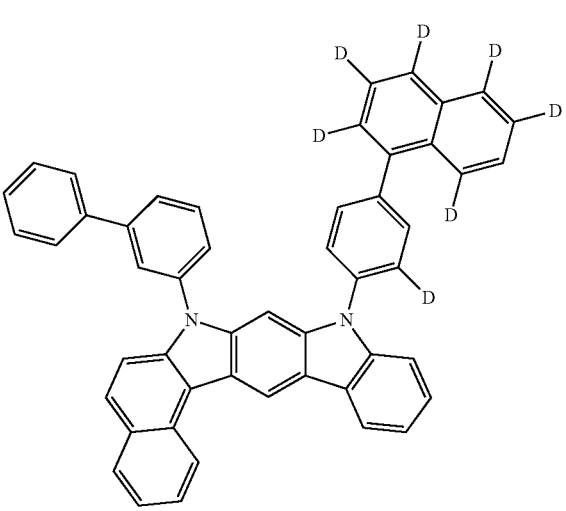
P-30
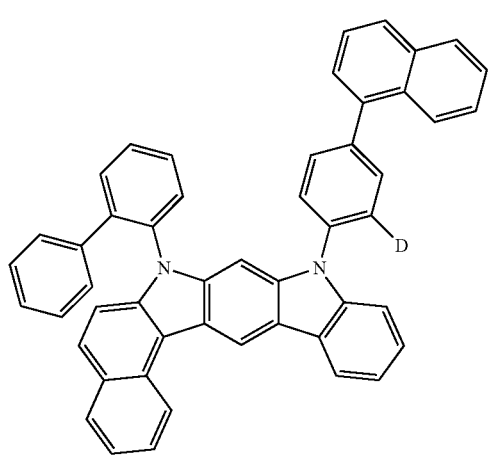

P-31
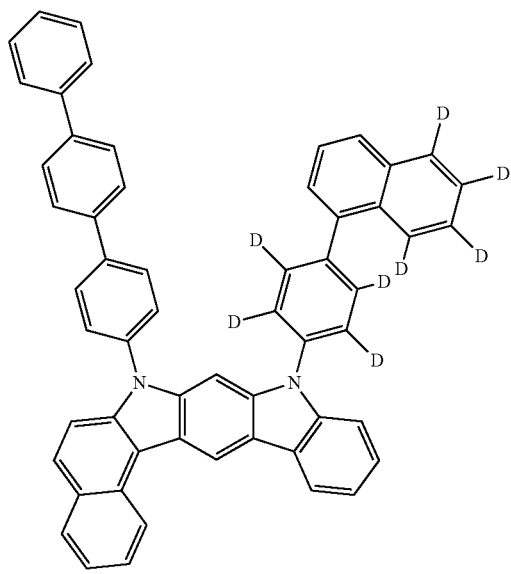
P-32
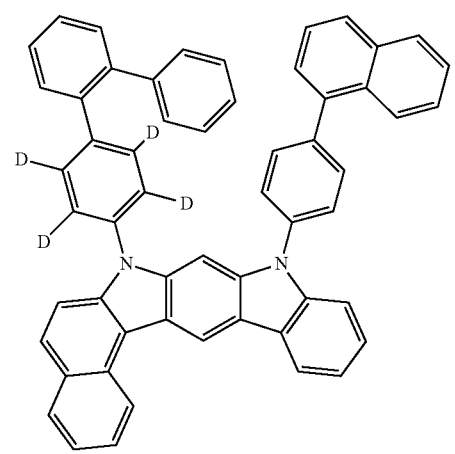
P-33
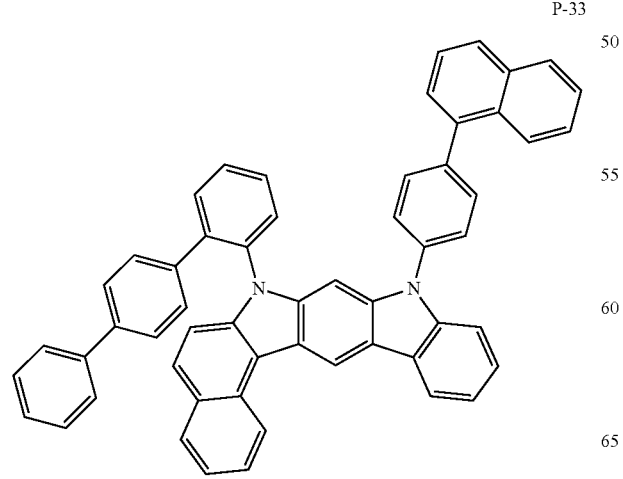
P-34
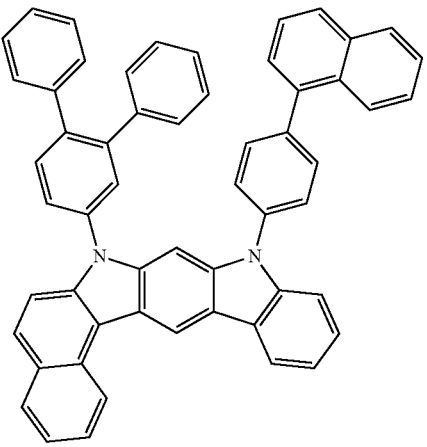
P-35
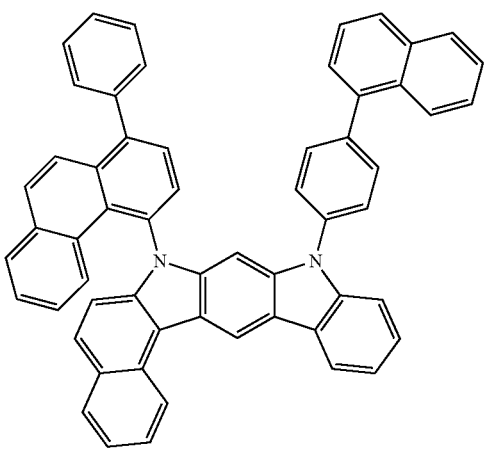
P-36
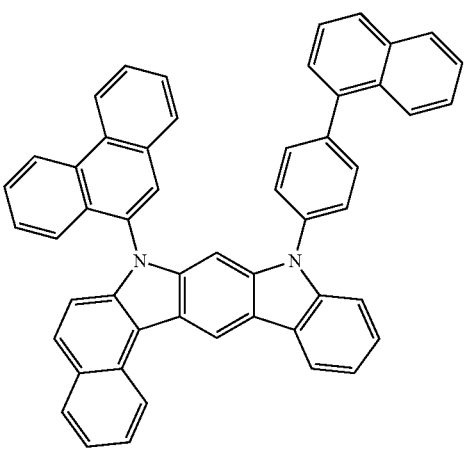

P-37
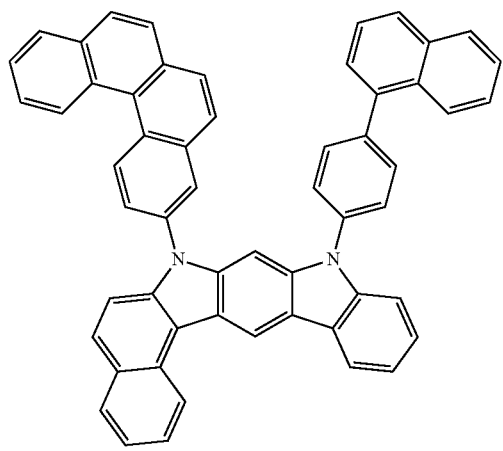
P-40
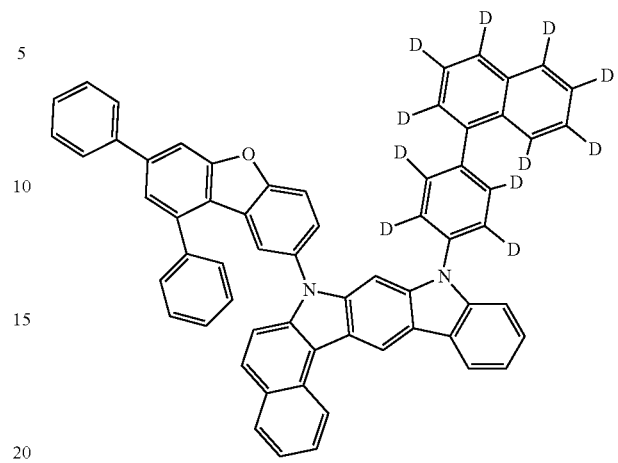
P-38
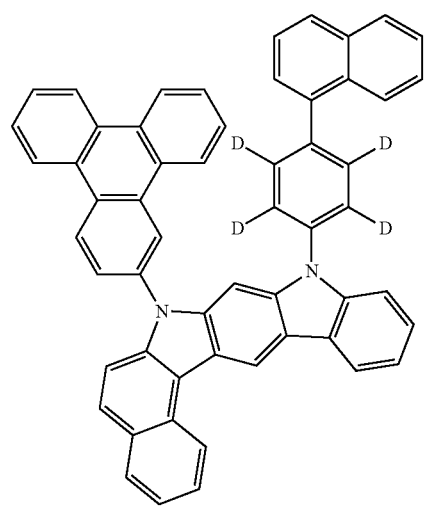
P-41
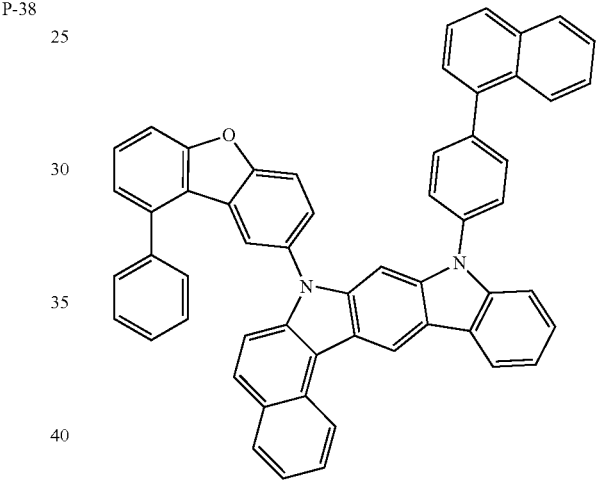
P-39
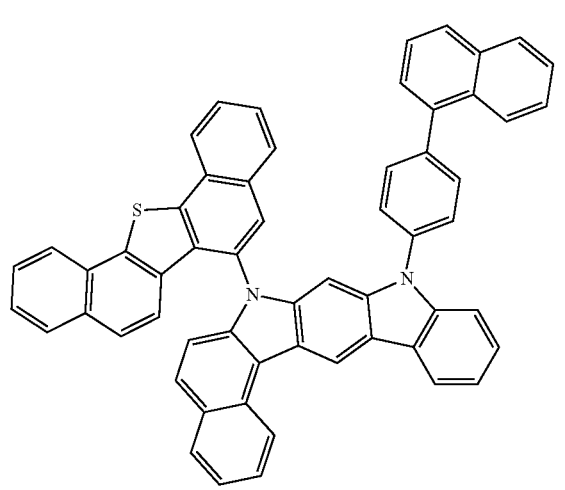
P-42
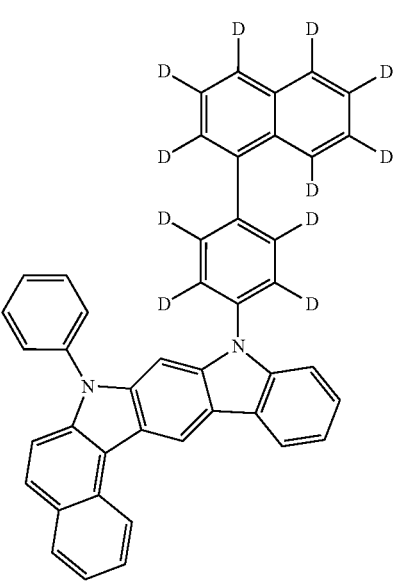

P-43
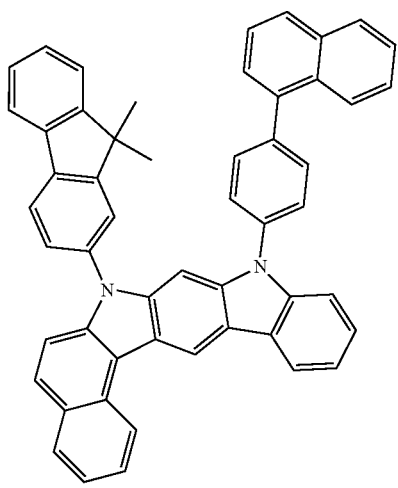
P-44
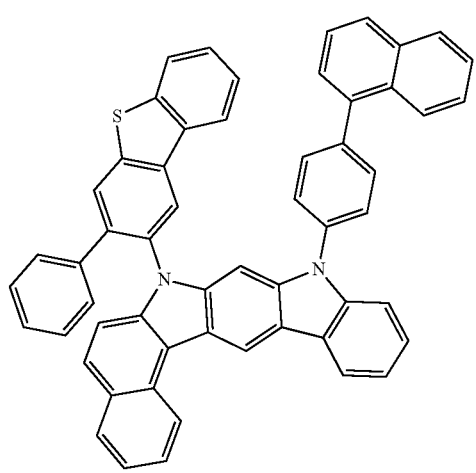
P-45
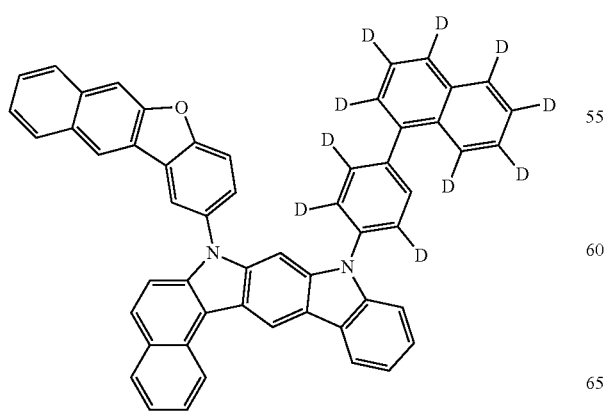
P-46
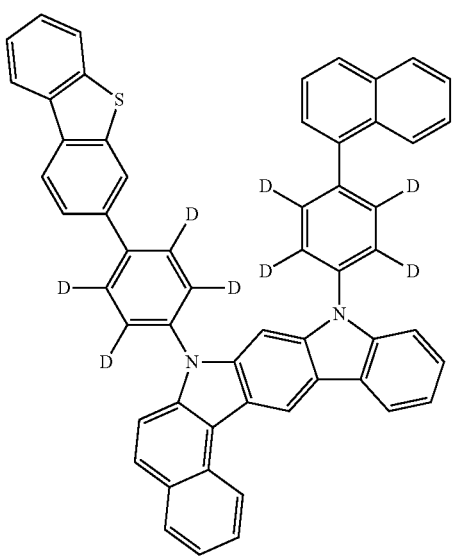
P-47
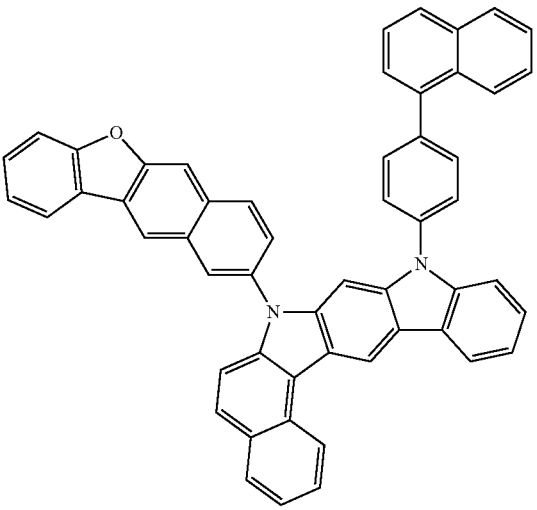
P-48
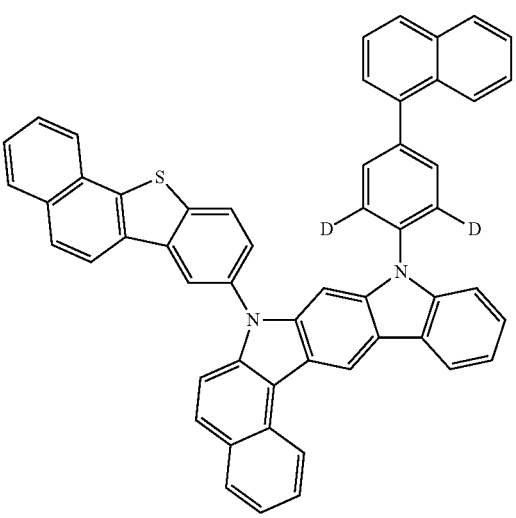

-continued
P-49
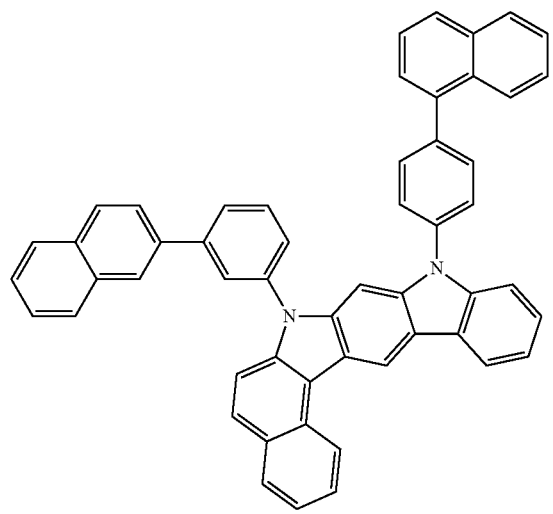
P-50
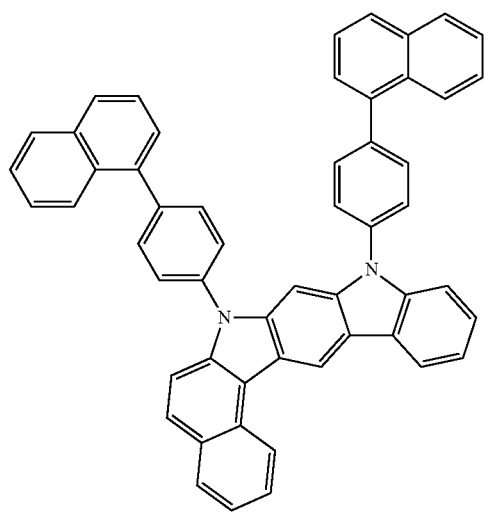
P-51
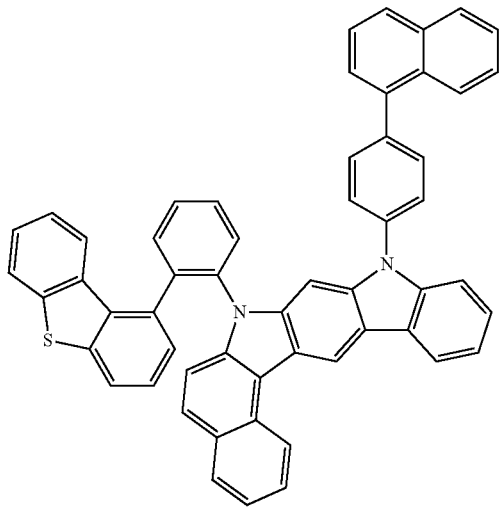
P-52
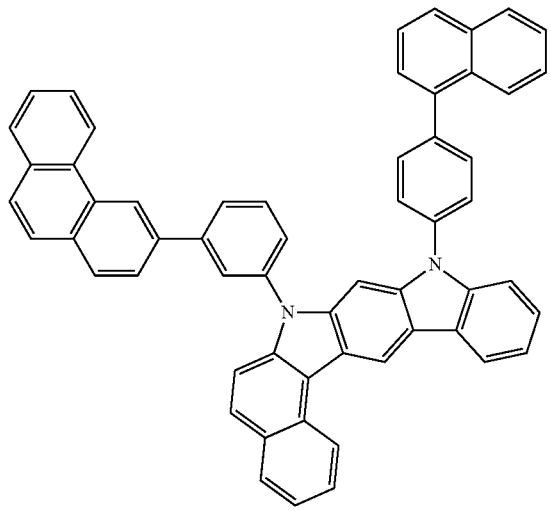
P-53
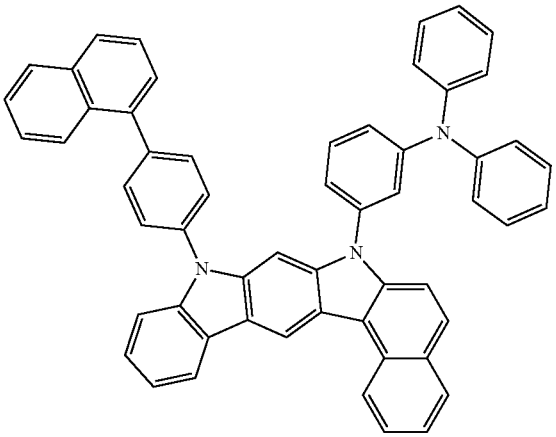
P-54
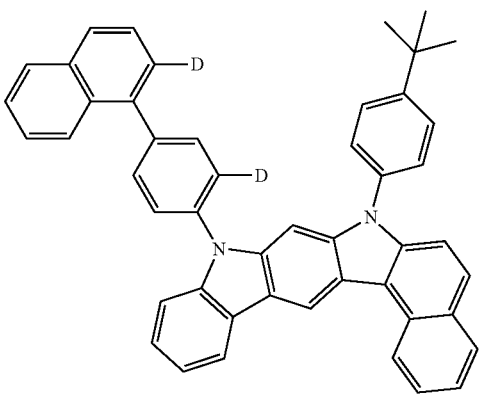

P-55
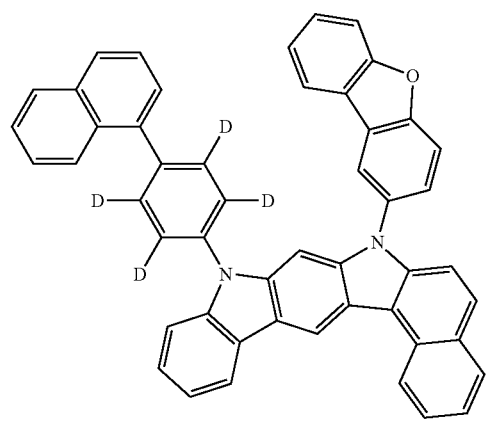

P-56
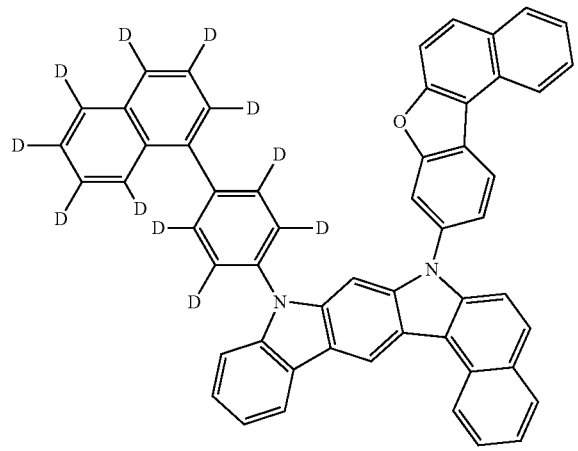

P-57
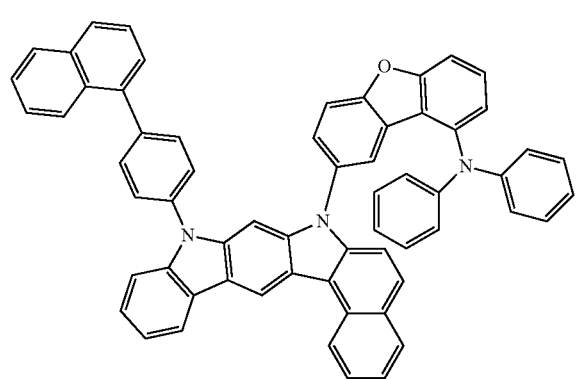

P-58
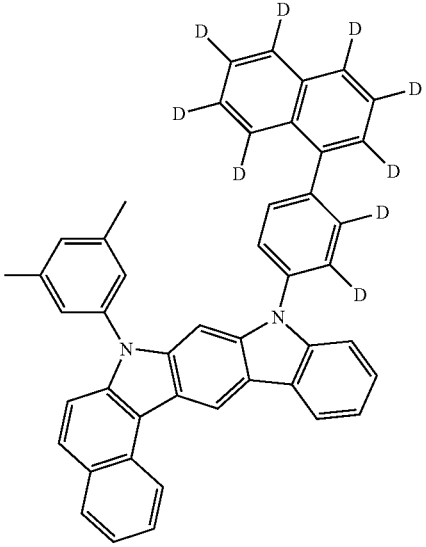

P-59
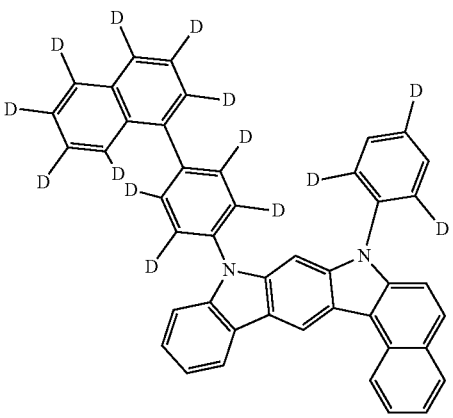

P-60
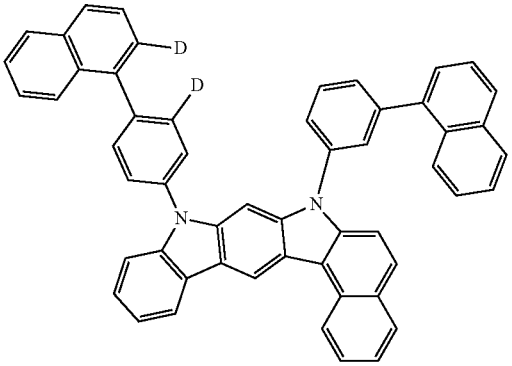

Figure 1:
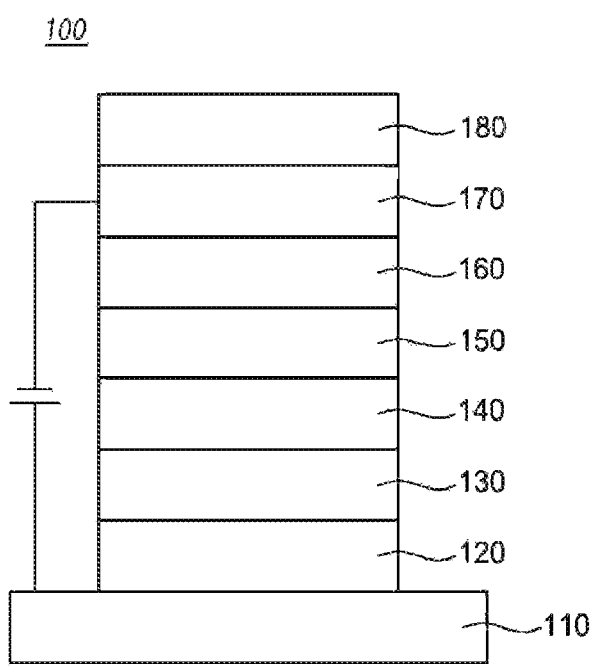
FIG. 1 to FIG. 3 are exemplary views of an organic electroluminescent device according to the present invention. The numbers used in the drawings represent.

Referring to FIG. 1, the organic electronic element (100) according to the present invention includes a first electrode (110), a second electrode (170), and an organic material layer including a single compound or 2 or more compounds represented by Formula 1 between the first electrode (110) and the second electrode (170). In this case, the first electrode (110) may be an anode, and the second electrode (170) may be a cathode. In the case of an inverted type, the first electrode may be a cathode and the second electrode may be an anode.

Figure 2:
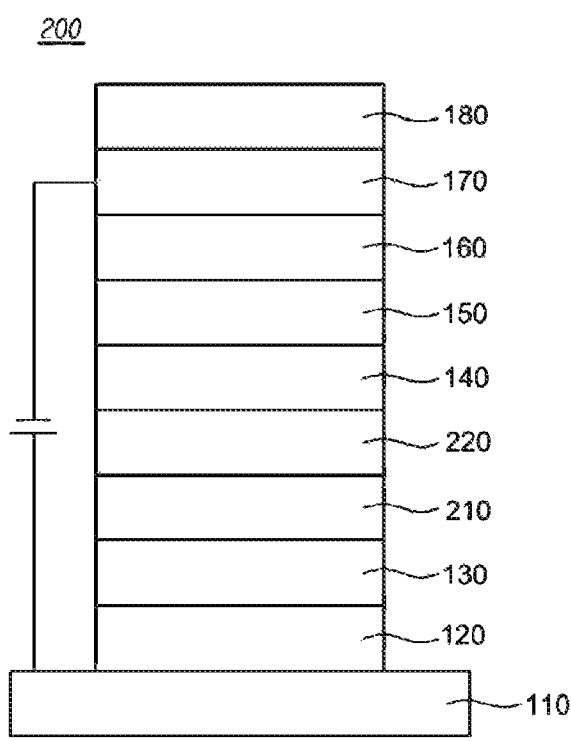

The organic material layer may sequentially include a hole injection layer (120), a hole transport layer (130), an emitting layer (140), an electron transport layer (150), and an electron injection layer (160) on the first electrode (110). In this case, the remaining layers except for the emitting layer (140) may not be formed. It may further include a hole blocking layer, an electron blocking layer, an emitting auxiliary layer (220), a buffer layer (210), etc. and the electron transport layer (150) and the like may serve as a hole blocking layer. (See FIG. 2)

Also, the organic electronic element according to an embodiment of the present invention may further include a protective layer or a light efficiency enhancing layer (180). The light efficiency enhancing layer may be formed on one of both surfaces of the first electrode not in contact with the organic material layer or on one of both surfaces of the second electrode not in contact with the organic material layer. The compound according to an embodiment of the present invention applied to the organic material layer may be used as a host or dopant of the hole injection layer (120), the hole transport layer (130), the emitting auxiliary layer (220), electron transport auxiliary layer, the electron transport layer (150), and an electron injection layer (160), the emitting layer (140) or as a material for the light efficiency enhancing layer. Preferably, for example, the compound according to Formula 1 of the present invention may be used as a host material of the emitting layer.

Figure 3:
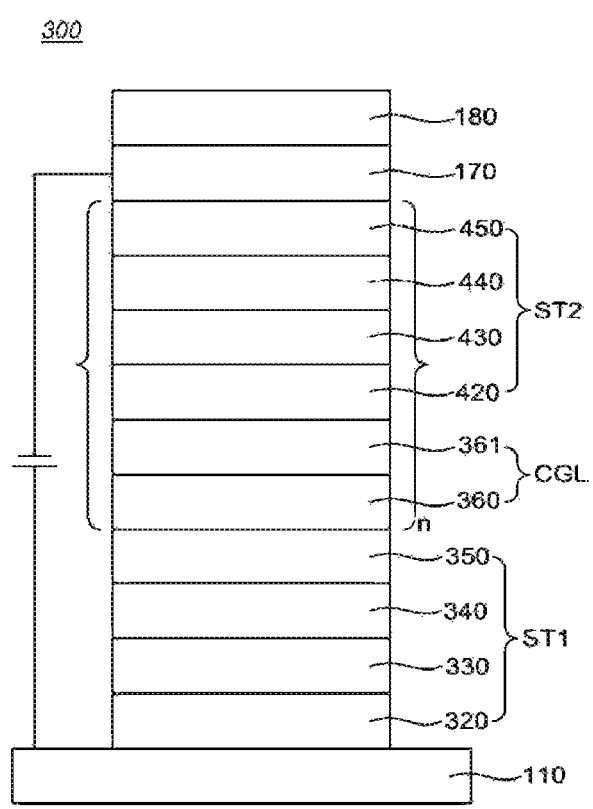

The organic material layer may include 2 or more stacks including a hole transport layer, an emitting layer and an electron transport layer sequentially formed on the anode, further include a charge generation layer formed between the 2 or more stacks (see FIG. 3).

Otherwise, even with the same core, the band gap, electrical characteristics, interface characteristics, etc. may vary depending on which position the substituent is bonded to, therefore the choice of core and the combination of sub-substituents bound thereto are also very important, and in particular, when the optimal combination of energy levels and T1 values and unique properties of materials (mobility, interfacial characteristics, etc.) of each organic material layer is achieved, a long lifespan and high efficiency can be achieved at the same time.

The organic electroluminescent device according to an embodiment of the present invention may be manufactured using a PVD (physical vapor deposition) method. For example, depositing a metal or a metal oxide having conductivity or an alloy thereof on a substrate to form an anode, and after forming an organic material layer including the hole injection layer (120), the hole transport layer (130), the emitting layer (140), the electron transport layer (150) and the electron injection layer (160) thereon, it can be prepared by depositing a material that can be used as a cathode thereon.

Also, in the present invention, the organic material layer is formed by any one of a spin coating process, a nozzle printing process, an inkjet printing process, a slot coating process, a dip coating process, and a roll-to-roll process, and the organic material layer provides an organic electric element comprising the compound as an emitting layer.

As another specific example, the same or different compounds of the compound represented by Formula (1) are mixed and used in the organic material layer.

Also, the present invention provides an emitting layer composition comprising the compound represented by Formula (1), and provides an organic electronic element comprising the emitting layer.

Also, the present invention provides an electronic device comprising a display device including the organic electronic element; and a control unit for driving the display device;

In another aspect, the organic electronic element is at least one of an organic electroluminescent device, an organic solar cell, an organic photoreceptor, an organic transistor, and a device for monochromatic or white lighting. At this time, the electronic device may be a current or future wired/wireless communication terminal, and covers all kinds of electronic devices including mobile communication terminals such as mobile phones, a personal digital assistant (PDA), an electronic dictionary, a point-to-multipoint (PMP), a remote controller, a navigation unit, a game player, various kinds of TVs, and various kinds of computers.

Hereinafter, a synthesis example of the compound represented by Formula (1) of the present invention and a manufacturing example of an organic electronic element of the present invention will be described in detail with reference to Examples, but the present invention is not limited to the following Examples.

SYNTHESIS EXAMPLES

The compound represented by Formula (1) according to the present invention (final products) is synthesized by reacting Sub 1 and Sub 2 as shown in Scheme 1 below, but is not limited thereto.

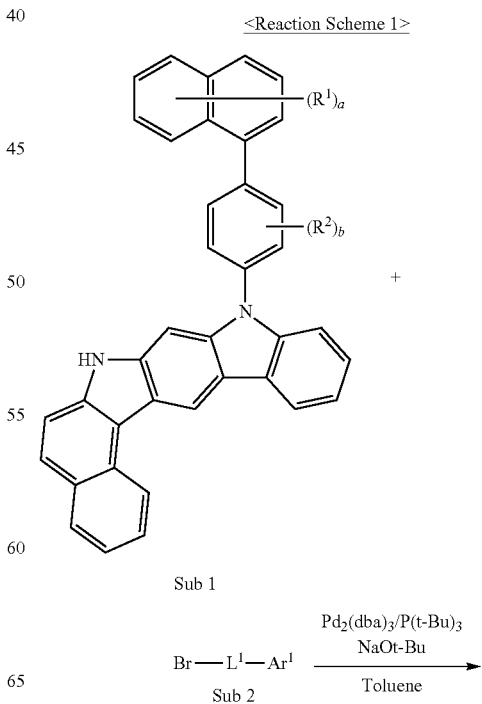

-continued

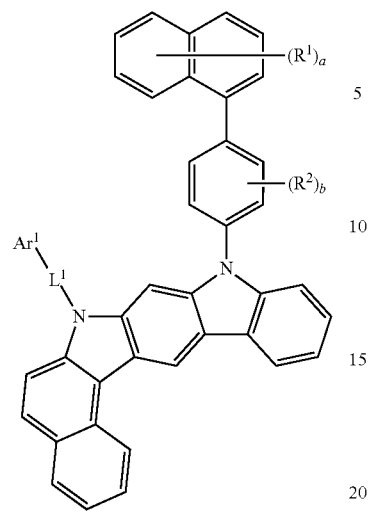

Final Products

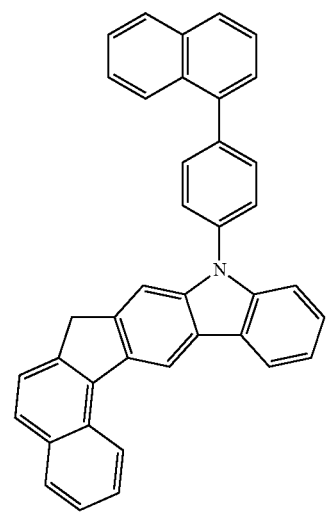

Sub1-1

1. Synthesis Example of Sub 1-1

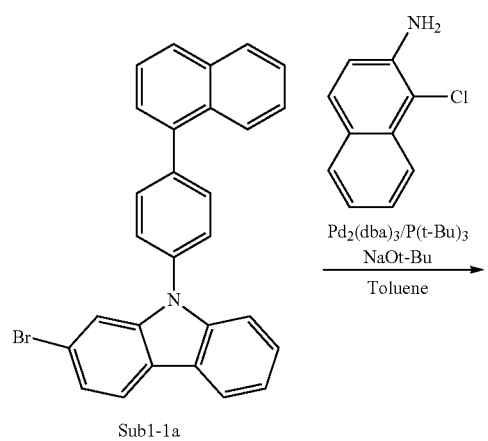

(1) Synthesis of Sub 1-1b

Sub 1-1a (50 g, 0.11 mol), 1-chloronaphthalen-2-amine (19.8 g, 0.11 mol), Pd$_2$(dba)$_3$ (3.1 g, 0.003 mol), 50% P(t-Bu)$_3$ (2.7 g, 0.007 mol), NaOt-Bu (32.2 g, 0.33 mol) were added to toluene (220 ml) and stirred at 90° C. After the reaction was completed, the reaction solvent was removed and the concentrated organic material was separated using a silica gel column or recrystallization method to obtain 50 g (88.3%) of Sub 1-1b product.

(2) Synthesis of Sub 1-1

Pd(OAc)$_2$ (0.62 g, 0.003 mol), P(t-Bu)$_3$ (2.2 g, 0.006 mol), K$_2$CO$_3$ (38 g, 0.28 mol), DMA (185 ml) were added to Sub 1-1 b (50 g, 0.09 mol) and stirred at 170° C. for 12 hours. When the reaction is complete, the reaction solvent is removed and put into ice water. Then, the precipitated solid was separated using a silica gel column or recrystallization method to obtain 28 g (60.1%) of the product Sub 1-1.

2. Synthesis Example of Sub 1-2

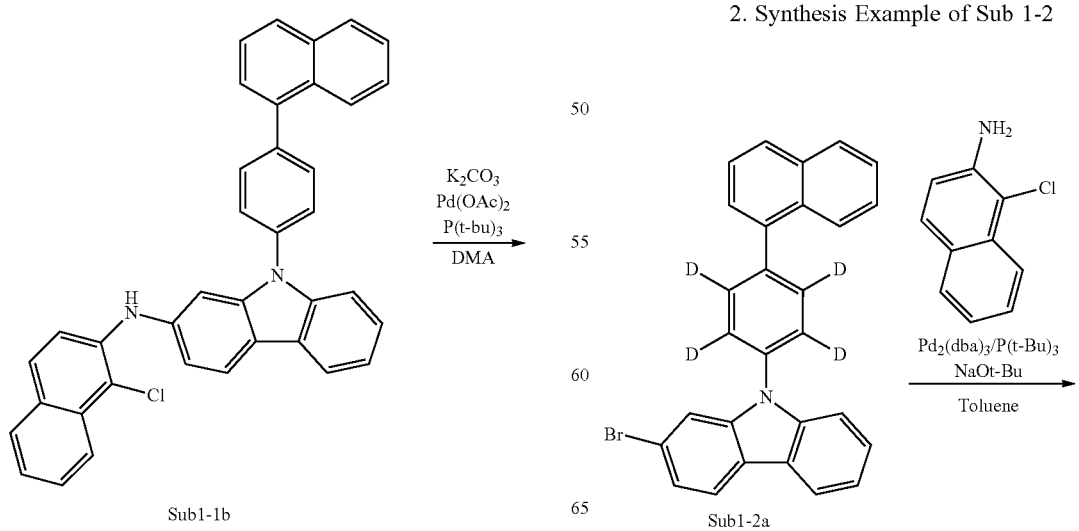

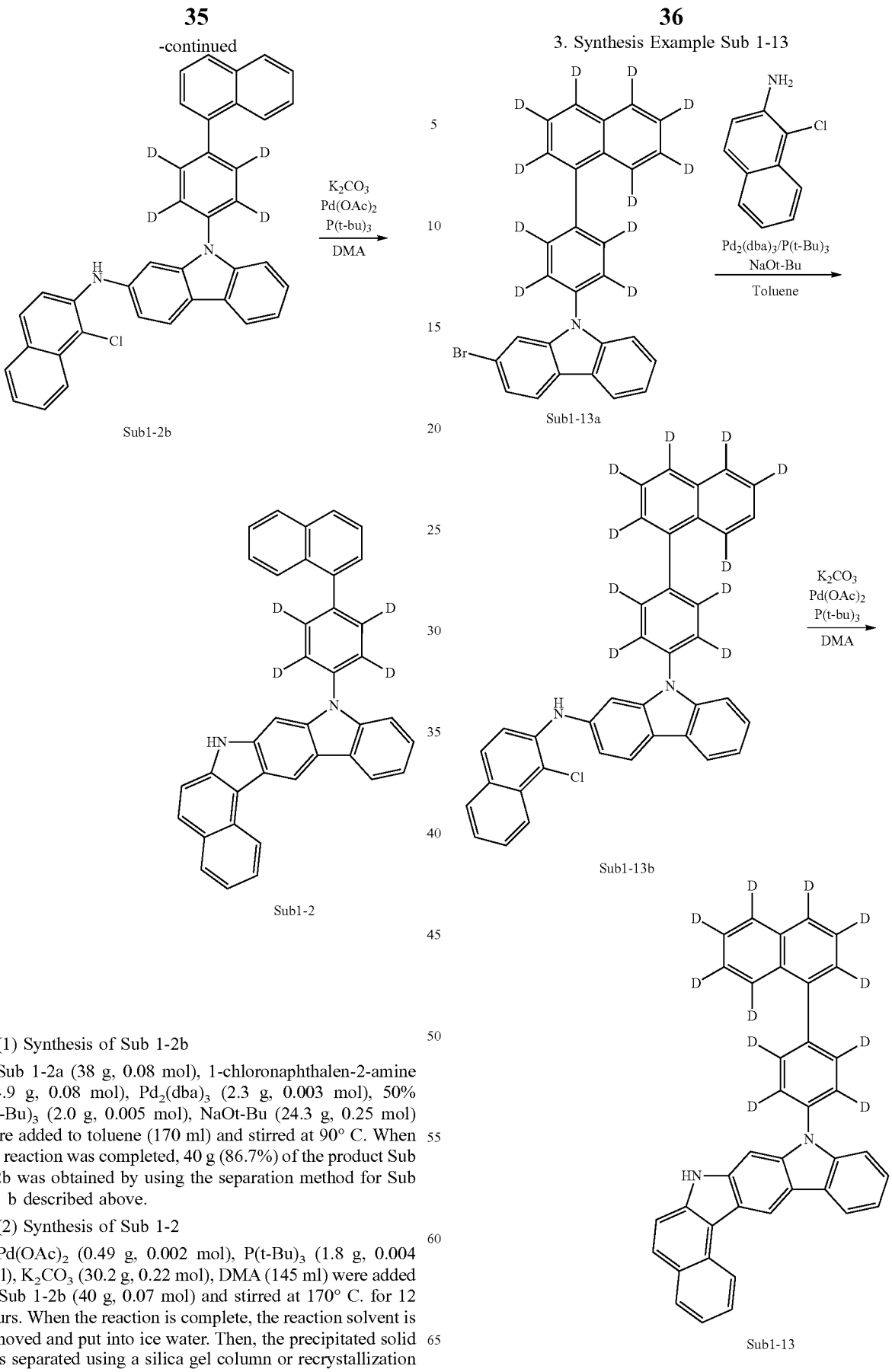

3. Synthesis Example Sub 1-13

(1) Synthesis of Sub 1-2b

Sub 1-2a (38 g, 0.08 mol), 1-chloronaphthalen-2-amine (14.9 g, 0.08 mol), $Pd_2(dba)_3$ (2.3 g, 0.003 mol), 50% $P(t-Bu)_3$ (2.0 g, 0.005 mol), NaOt-Bu (24.3 g, 0.25 mol) were added to toluene (170 ml) and stirred at 90° C. When the reaction was completed, 40 g (86.7%) of the product Sub 1-2b was obtained by using the separation method for Sub 1-1 b described above.

(2) Synthesis of Sub 1-2

$Pd(OAc)_2$ (0.49 g, 0.002 mol), $P(t-Bu)_3$ (1.8 g, 0.004 mol), $K_2CO_3$ (30.2 g, 0.22 mol), DMA (145 ml) were added to Sub 1-2b (40 g, 0.07 mol) and stirred at 170° C. for 12 hours. When the reaction is complete, the reaction solvent is removed and put into ice water. Then, the precipitated solid was separated using a silica gel column or recrystallization method to obtain 23 g (61.7%) of the product Sub 1-2.

(1) Synthesis of Sub 1-13b

Sub 1-13a (50 g, 0.11 mol), 1-chloronaphthalen-2-amine (19.3 g, 0.11 mol), Pd$_2$(dba)$_3$ (3.0 g, 0.003 mol), 50% P(t-Bu)$_3$ (2.6 g, 0.007 mol), NaOt-Bu (31.4 g, 0.33 mol) were added to toluene (220 ml) and stirred at 90° C. When the reaction was completed, 51 g (84.2%) of the product Sub 1-13b was obtained by using the separation method for Sub 1-1b.

(2) Synthesis of Sub 1-13

Pd(OAc)$_2$ (0.48 g, 0.002 mol), P(t-Bu)$_3$ (1.7 g, 0.004 mol), K$_2$CO$_3$ (29.8 g, 0.22 mol), DMA (145 ml) were added to Sub 1-13b (40 g, 0.07 mol) and stirred at 170° C. for 12 hours. When the reaction is complete, the reaction solvent is removed and put into ice water. Then, the precipitated solid was separated using a silica gel column or recrystallization method to obtain 24 g (64.3%) of the product Sub 1-13.

Meanwhile, the compound belonging to Sub 1 may be the following compounds, but is not limited thereto, and Table 1 below shows FD-MS (Field Desorption-Mass Spectrometry) values of the compounds belonging to Sub 1-1 to Sub 1-13.

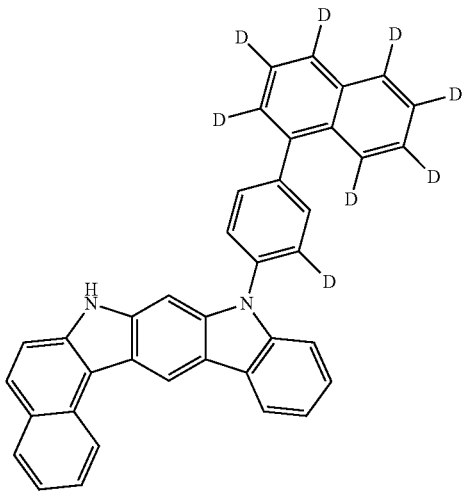

Sub1-3

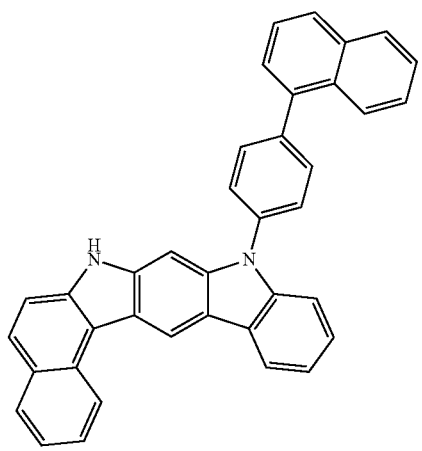

Sub1-1

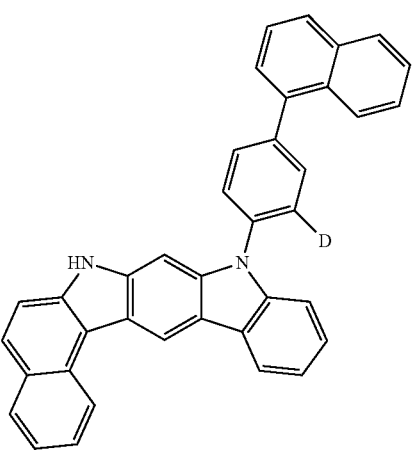

Sub1-4

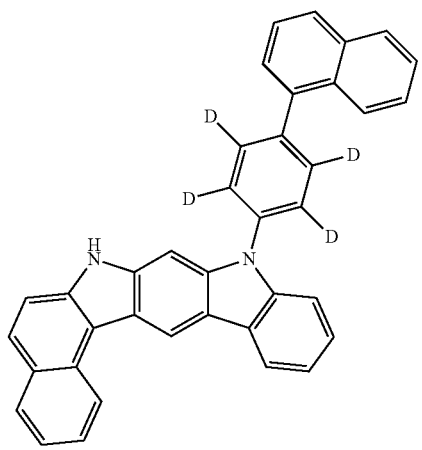

Sub1-2

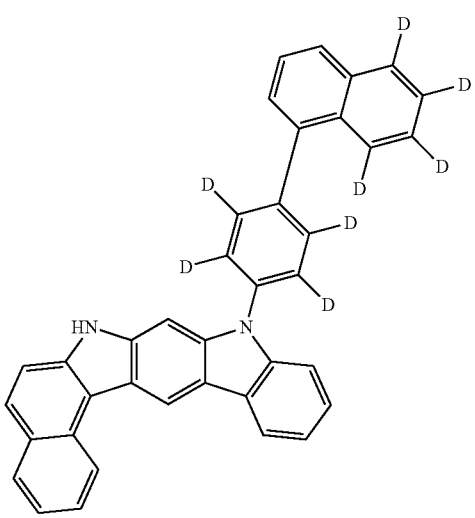

Sub1-5

Sub1-6
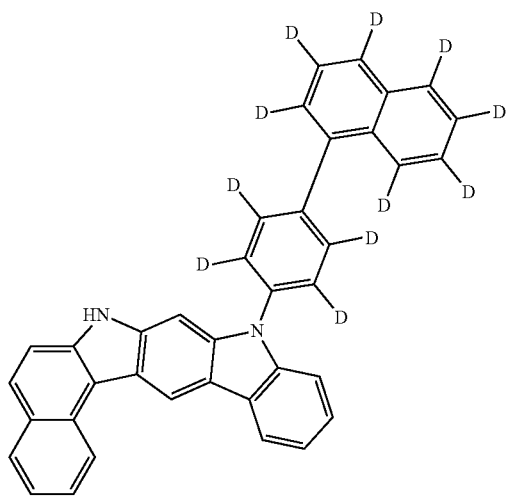
Sub1-7
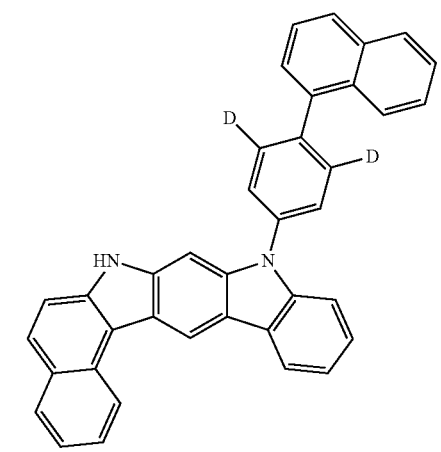
Sub1-8
Sub1-9
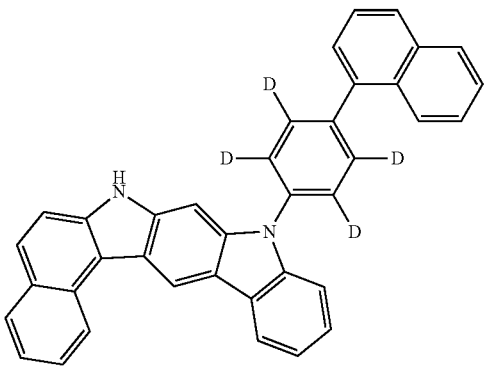
Sub1-10
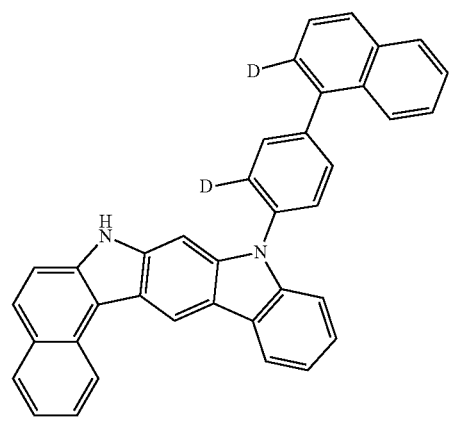
Sub1-11
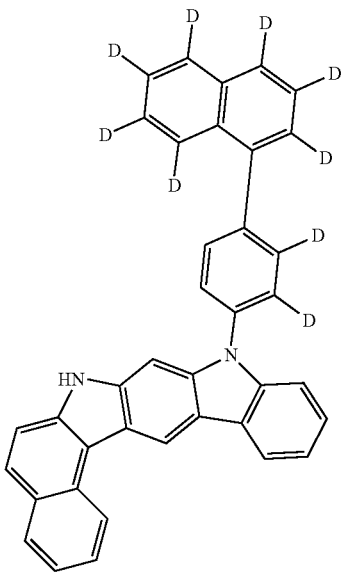

Sub1-12

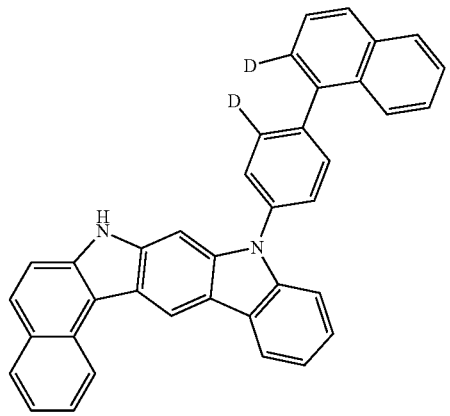

Sub1-13

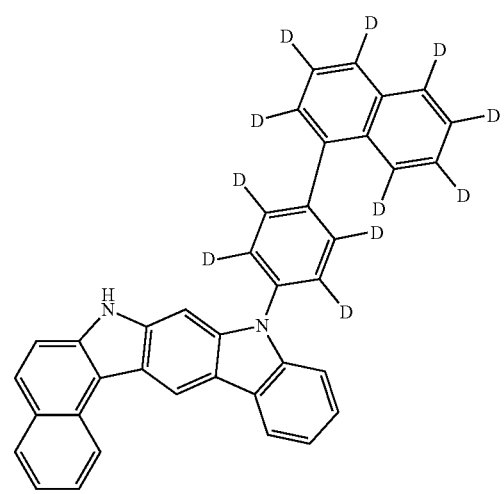

Sub2-2

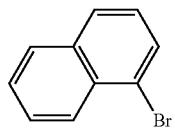

Sub2-3

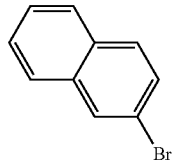

Sub2-4

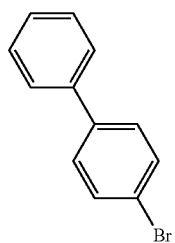

Sub2-5

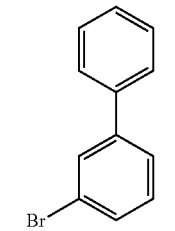

TABLE

| compound | FD-MS | compound | FD-MS |
|---|---|---|---|
| Sub 1-1 | m/z = 508.19($C_{38}H_{24}N_2$ = 508.62) | Sub 1-2 | m/z = 512.22($C_{38}H_{20}D_4N_2$ = 512.65) |
| Sub 1-3 | m/z = 516.24($C_{38}H_{16}D_8N_2$ = 516.67) | Sub 1-4 | m/z = 509.2($C_{38}H_{23}DN_2$ = 509.63) |
| Sub 1-5 | m/z = 516.24($C_{38}H_{16}D_8N_2$ = 516.67) | Sub 1-6 | m/z = 518.26($C_{38}H_{14}D_{10}N_2$ = 518.69) |
| Sub 1-7 | m/z = 510.21($C_{38}H_{22}D_2N_2$ = 510.64) | Sub 1-8 | m/z = 510.21($C_{38}H_{22}D_2N_2$ = 510.64) |
| Sub 1-9 | m/z = 512.22($C_{38}H_{20}D_4N_2$ = 512.65) | Sub 1-10 | m/z = 510.21($C_{38}H_{22}D_2N_2$ = 510.64) |
| Sub 1-11 | m/z = 517.25($C_{38}H_{15}D_9N_2$ = 517.68) | Sub 1-12 | m/z = 510.21($C_{38}H_{22}D_2N_2$ = 510.64) |
| Sub 1-13 | m/z = 519.26($C_{38}H_{13}D_{11}N_2$ = 519.69) | | |

Meanwhile, the compound belonging to Sub 2 may be a compound as follows, but is not limited thereto, and Table 2 below shows Field Desorption-Mass Spectrometry (FD-MS) values of the compound belonging to Sub 2-1 to Sub 2-52.

Sub2-1

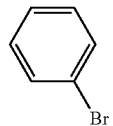

Sub2-6

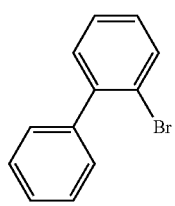

Sub2-7
Sub2-8
Sub2-9
Sub2-10
Sub2-11
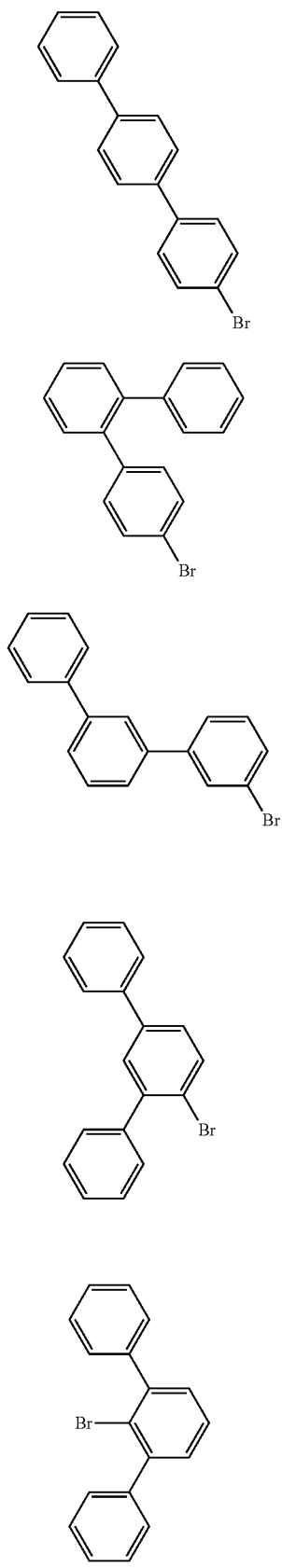
Sub2-12
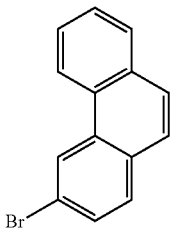
Sub2-13
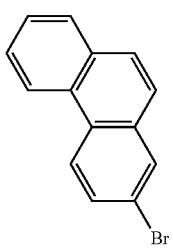
Sub2-14
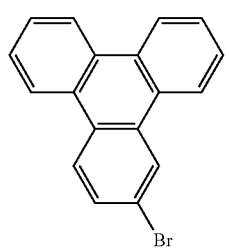
Sub2-15
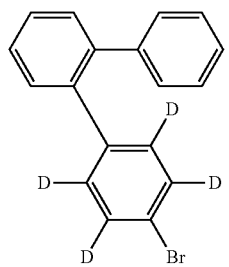
Sub2-16
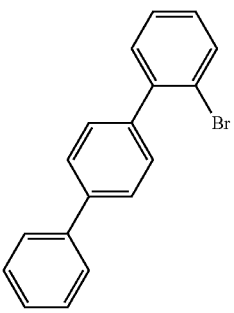
Sub2-17
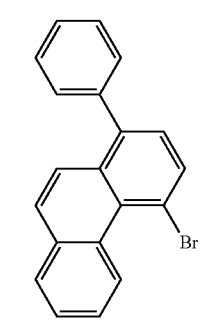

Sub2-18
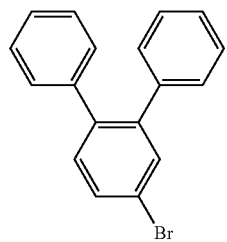
Sub2-25
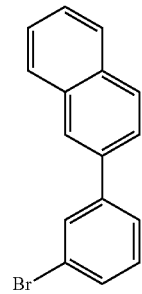
Sub2-26
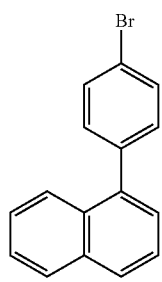
Sub2-27
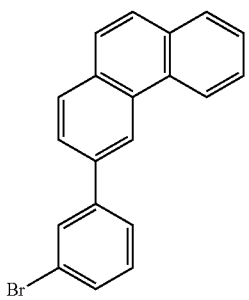
Sub2-28
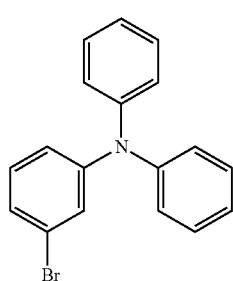
Sub2-29
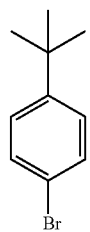
Sub2-30
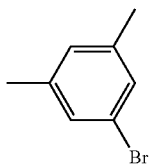
Sub2-31
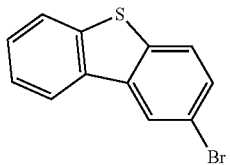
Sub2-32
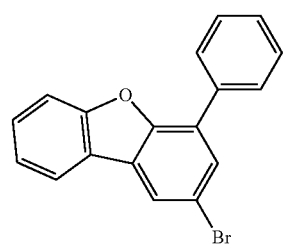
Sub2-33
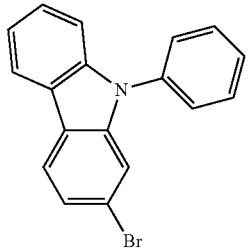
Sub2-34
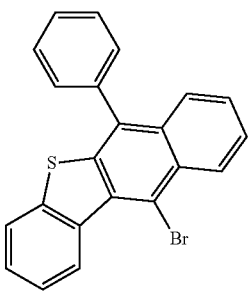
Sub2-35
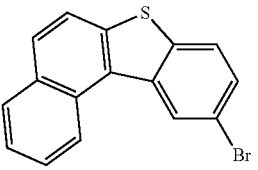

Sub2-36
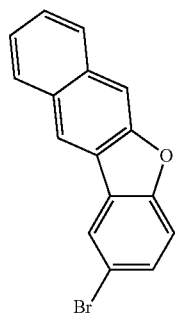
Sub2-37
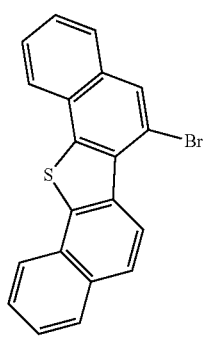
Sub2-38
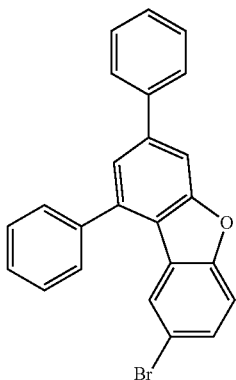
Sub2-39
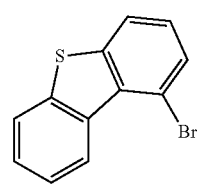
Sub2-40
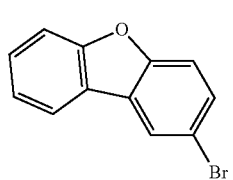
Sub2-41
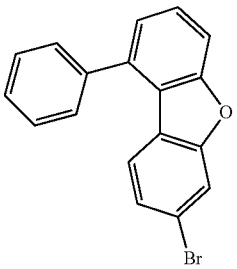
Sub2-42
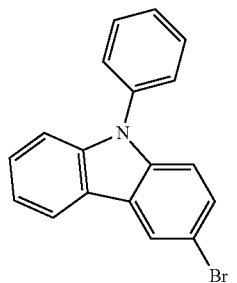
Sub2-43
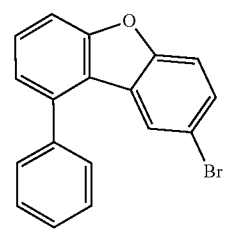
Sub2-44
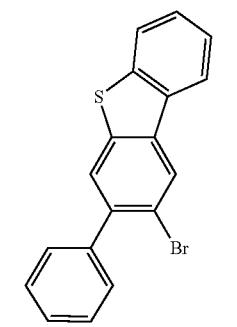
Sub2-45
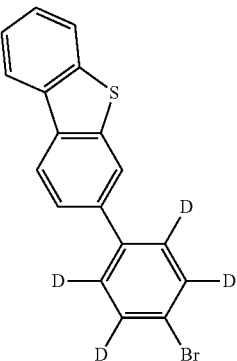

Sub2-46

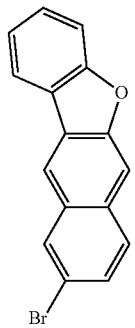

Sub2-47

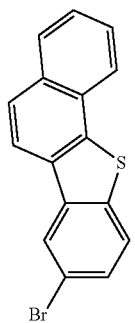

Sub2-48

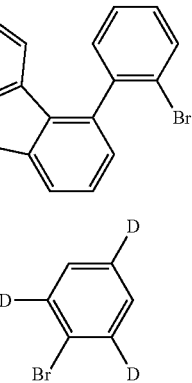

Sub2-49

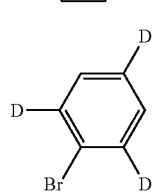

Sub2-50

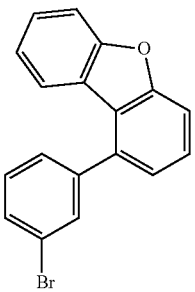

Sub2-51

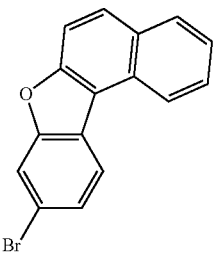

Sub2-52

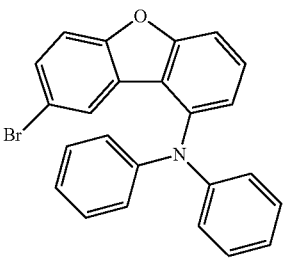

TABLE 2

| compound | FD-MS | compound | FD-MS |
|---|---|---|---|
| Sub 2-1 | m/z = 155.96($C_6H_5Br$ = 157.01) | Sub 2-2 | m/z = 205.97($C_{10}H_7Br$ = 207.07) |
| Sub 2-3 | m/z = 205.97($C_{10}H_7Br$ = 207.07) | Sub 2-4 | m/z = 231.99($C_{12}H_9Br$ = 233.11) |
| Sub 2-5 | m/z = 231.99($C_{12}H_9Br$ = 233.11) | Sub 2-6 | m/z = 231.99($C_{12}H_9Br$ = 233.11) |
| Sub 2-7 | m/z = 308.02($C_{18}H_{13}Br$ = 309.21) | Sub 2-8 | m/z = 308.02($C_{18}H_{13}Br$ = 309.21) |
| Sub 2-9 | m/z = 308.02($C_{18}H_{13}Br$ = 309.21) | Sub 2-10 | m/z = 308.02($C_{18}H_{13}Br$ = 309.21) |
| Sub 2-11 | m/z = 308.02($C_{18}H_{13}Br$ = 309.21) | Sub 2-12 | m/z = 255.99($C_{14}H_9Br$ = 257.13) |
| Sub 2-13 | m/z = 255.99($C_{14}H_9Br$ = 257.13) | Sub 2-14 | m/z = 306($C_{18}H_{11}Br$ = 307.19) |
| Sub 2-15 | m/z = 312.05($C_{18}H_9D_4Br$ = 313.23) | Sub 2-16 | m/z = 308.02($C_{18}H_{13}Br$ = 309.21) |
| Sub 2-17 | m/z = 332.02($C_{20}H_{13}Br$ = 333.23) | Sub 2-18 | m/z = 308.02($C_{18}H_{13}Br$ = 309.21) |
| Sub 2-19 | m/z = 282($C_{16}H_{11}Br$ = 283.17) | Sub 2-20 | m/z = 272.02($C_{15}H_{13}Br$ = 273.17) |
| Sub 2-21 | m/z = 255.99($C_{14}H_9Br$ = 257.13) | Sub 2-22 | m/z = 306($C_{18}H_{11}Br$ = 307.19) |
| Sub 2-23 | m/z = 306($C_{18}H_{11}Br$ = 307.19) | Sub 2-24 | m/z = 272.02($C_{15}H_{13}Br$ = 273.17) |
| Sub 2-25 | m/z = 282($C_{16}H_{11}Br$ = 283.17) | Sub 2-26 | m/z = 282($C_{16}H_{11}Br$ = 283.17) |
| Sub 2-27 | m/z = 332.02($C_{20}H_{13}Br$ = 333.23) | Sub 2-28 | m/z = 323.03($C_{18}H_{14}BrN$ = 324.22) |
| Sub 2-29 | m/z = 212.02($C_{10}H_{13}Br$ = 213.12) | Sub 2-30 | m/z = 183.99($C_8H_9Br$ = 185.06) |
| Sub 2-31 | m/z = 261.95($C_{12}H_7BrS$ = 263.15) | Sub 2-32 | m/z = 322($C_{18}H_{11}BrO$ = 323.19) |
| Sub 2-33 | m/z = 321.02($C_{18}H_{12}BrN$ = 322.21) | Sub 2-34 | m/z = 387.99($C_{22}H_{13}BrS$ = 389.31) |
| Sub 2-35 | m/z = 311.96($C_{16}H_9BrS$ = 313.21) | Sub 2-36 | m/z = 295.98($C_{16}H_9BrO$ = 297.15) |
| Sub 2-37 | m/z = 361.98($C_{20}H_{11}BrS$ = 363.27) | Sub 2-38 | m/z = 398.03($C_{24}H_{15}BrO$ = 399.29) |
| Sub 2-39 | m/z = 261.95($C_{12}H_7BrS$ = 263.15) | Sub 2-40 | m/z = 245.97($C_{12}H_7BrO$ = 247.09) |
| Sub 2-41 | m/z = 322($C_{18}H_{11}BrO$ = 323.19) | Sub 2-42 | m/z = 321.02($C_{18}H_{12}BrN$ = 322.21) |
| Sub 2-43 | m/z = 322($C_{18}H_{11}BrO$ = 323.19) | Sub 2-44 | m/z = 337.98($C_{18}H_{11}BrS$ = 339.25) |
| Sub 2-45 | m/z = 342($C_{18}H_7D_4BrS$ = 343.27) | Sub 2-46 | m/z = 295.98($C_{16}H_9BrO$ = 297.15) |

TABLE 2-continued

| compound | FD-MS | compound | FD-MS |
|---|---|---|---|
| Sub 2-47 | m/z = 311.96($C_{16}H_9BrS$ = 313.21) | Sub 2-48 | m/z = 337.98($C_{18}H_{11}BrS$ = 339.25) |
| Sub 2-49 | m/z = 158.98($C_6H_2D_3Br$ = 160.03) | Sub 2-50 | m/z = 322($C_{18}H_{11}BrO$ = 323.19) |
| Sub 2-51 | m/z = 295.98($C_{16}H_9BrO$ = 297.15) | Sub 2-52 | m/z = 413.04($C_{24}H_{16}BrNO$ = 414.3) |

II. Synthesis of Final Products

1. Synthesis Example of P-1

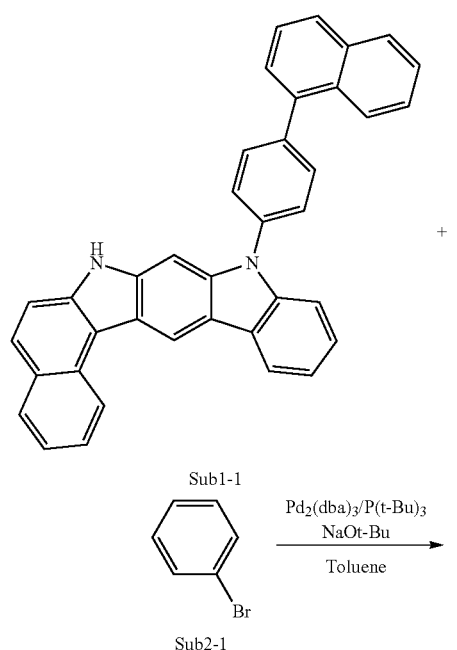

2. Synthesis Example of P-7

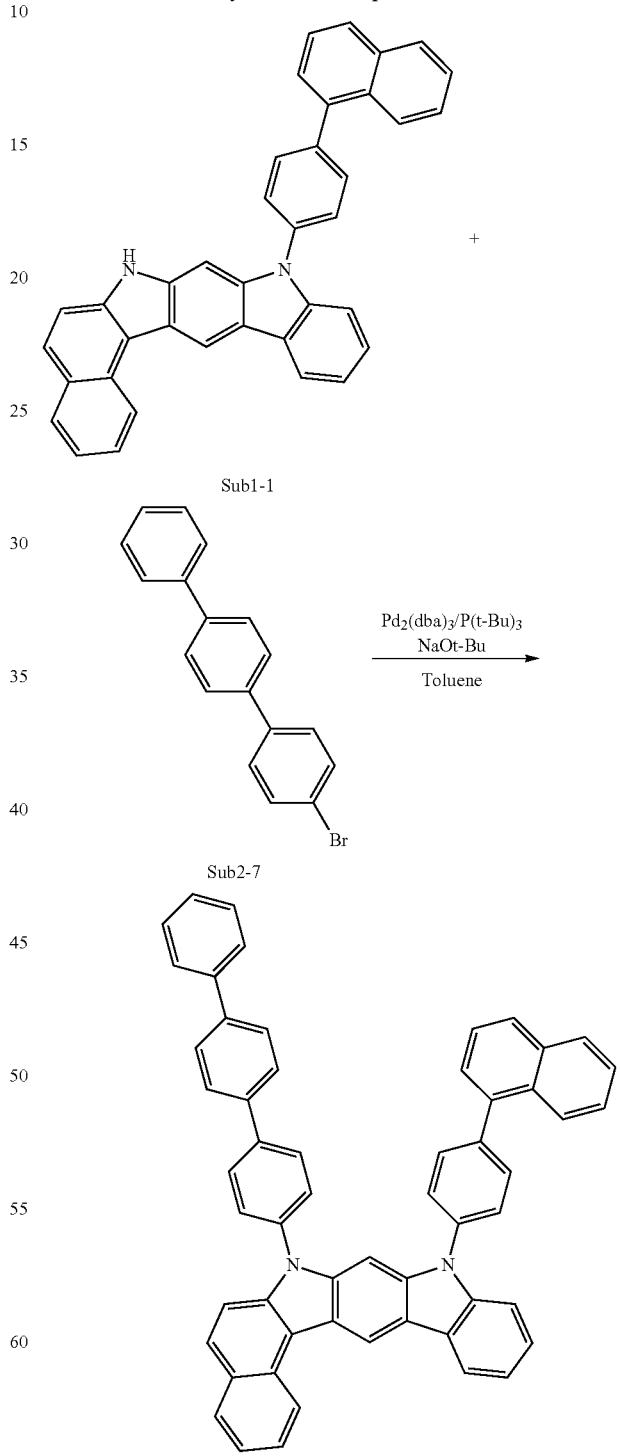

Sub 1-1 (30 g, 0.06 mol), Sub2-1 (9.3 g, 0.06 mol), Pd$_2$(dba)$_3$ (1.6 g, 0.002 mol), NaOt-Bu (16.9 g, 0.18 mol), P(t-Bu)$_3$ (1.4 g, 0.004 mol), Toluene (120 mL) were added and reacted at 135° C. for 6 hours. When the reaction is completed, the temperature of the reactant is cooled to room temperature, and the reaction solvent is removed. Then, the concentrated reactant was separated using a silica gel column or recrystallization method to obtain 28 g (81.3%) of product P-1.

Sub 1-1 (50 g, 0.10 mol), Sub 2-7 (30.4 g, 0.10 mol), Pd$_2$(dba)$_3$ (2.7 g, 0.003 mol), NaOt-Bu (28.4 g, 0.29 mol), P(t-Bu)$_3$ (2.4 g, 0.006 mol), Toluene (200 mL) were added and reacted at 135° C. for 6 hours. When the reaction was completed, 59 g (81.5%) of product P-7 was obtained by using the separation method for P-1.

3. Synthesis Example of P-12

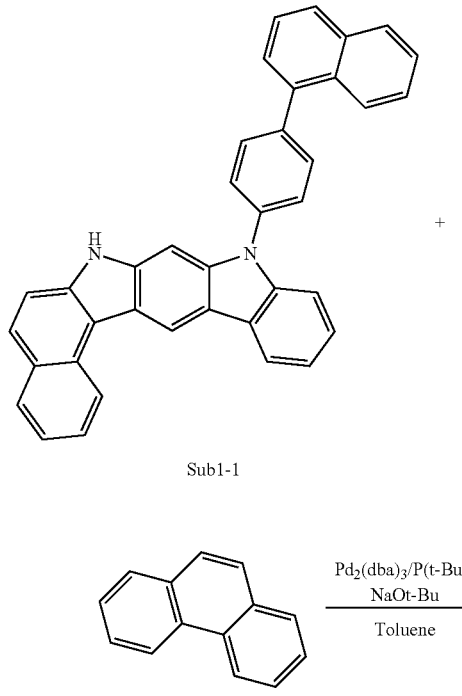

4. Synthesis Example of P-20

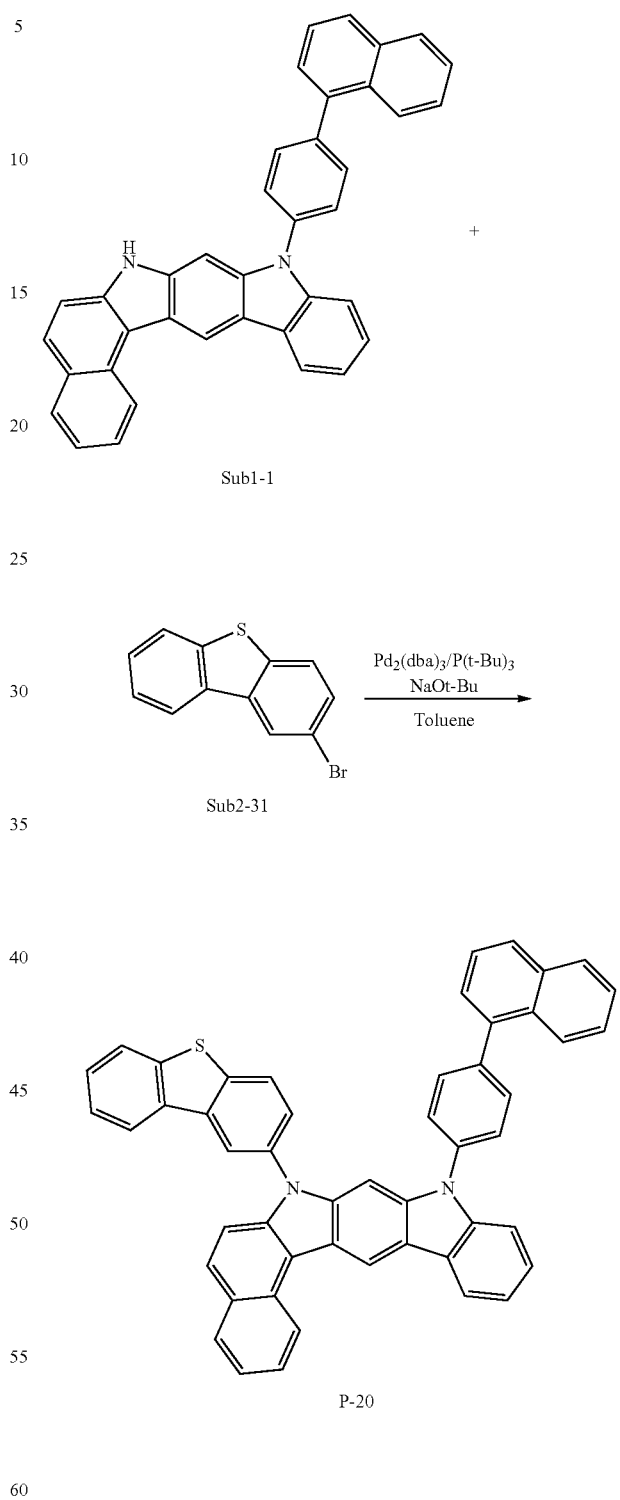

Sub 1-1 (20 g, 0.04 mol), Sub 2-12 (10.1 g, 0.04 mol), Pd$_2$(dba)$_3$ (1.1 g, 0.001 mol), NaOt-Bu (11.3 g, 0.12 mol), P(t-Bu)$_3$ (1.0 g, 0.0024 mol), Toluene (80 mL) were added and reacted at 135° C. for 6 hours. When the reaction was completed, 24 g (89.2%) of product P-12 was obtained by using the separation method for P-1.

Sub 1-1 (30 g, 0.06 mol), Sub 2-31 (15.5 g, 0.06 mol), Pd$_2$(dba)$_3$ (1.6 g, 0.002 mol), NaOt-Bu (17 g, 0.18 mol), P(t-Bu)$_3$ (1.4 g, 0.0035 mol), Toluene (120 mL) were added and reacted at 135° C. for 6 hours. When the reaction was completed, 35 g (86%) of product P-20 was obtained by using the separation method for P-1.

5. Synthesis Example of P-25

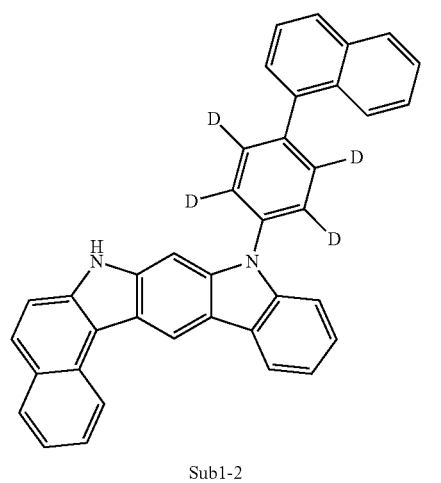

Sub1-2

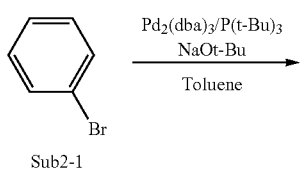

Sub2-1

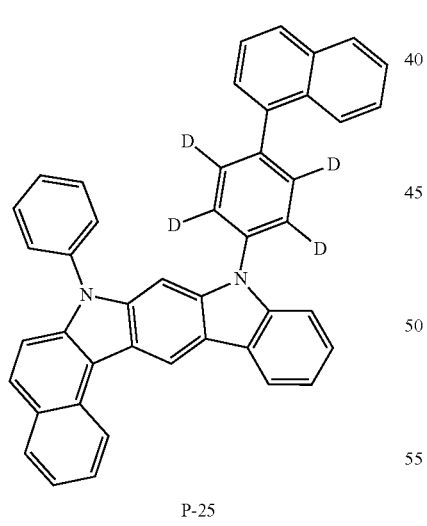

P-25

Sub 1-2 (15 g, 0.03 mol), Sub 2-1 (4.6 g, 0.03 mol), Pd$_2$(dba)$_3$ (0.8 g, 0.0009 mol), NaOt-Bu (8.5 g, 0.09 mol), P(t-Bu)$_3$ (0.7 g, 0.0018 mol), Toluene (60 mL) were added and reacted at 135° C. for 6 hours. When the reaction was completed, 16 g (92.9%) of product P-25 was obtained by using the separation method for P-1.

6. Synthesis Example of P-42

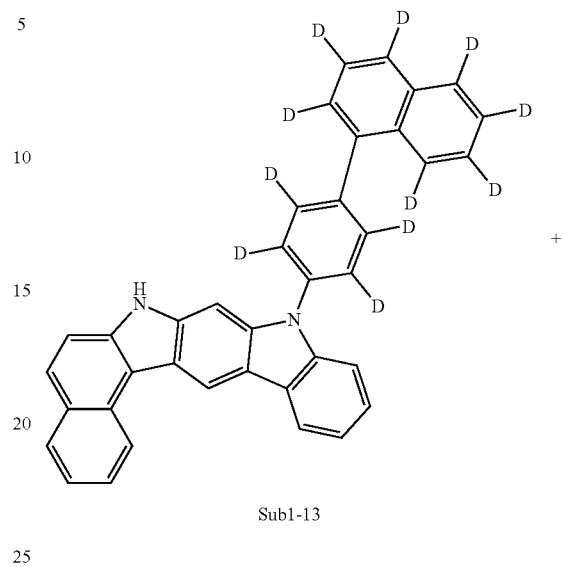

Sub1-13

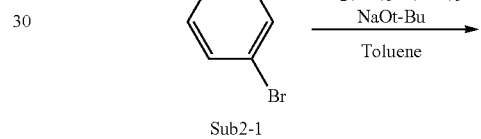

Sub2-1

P-42

Sub 1-13 (20 g, 0.04 mol), Sub 2-1 (6.1 g, 0.04 mol), Pd$_2$(dba)$_3$ (1.1 g, 0.0012 mol), NaOt-Bu (11.1 g, 0.12 mol), P(t-Bu)$_3$ (0.9 g, 0.0023 mol), Toluene (80 mL) were added and reacted at 135° C. for 6 hours. When the reaction was completed, 20 g (87.2%) of product P-42 was obtained by using the separation method for P-1.

7. Synthesis Example of P-53

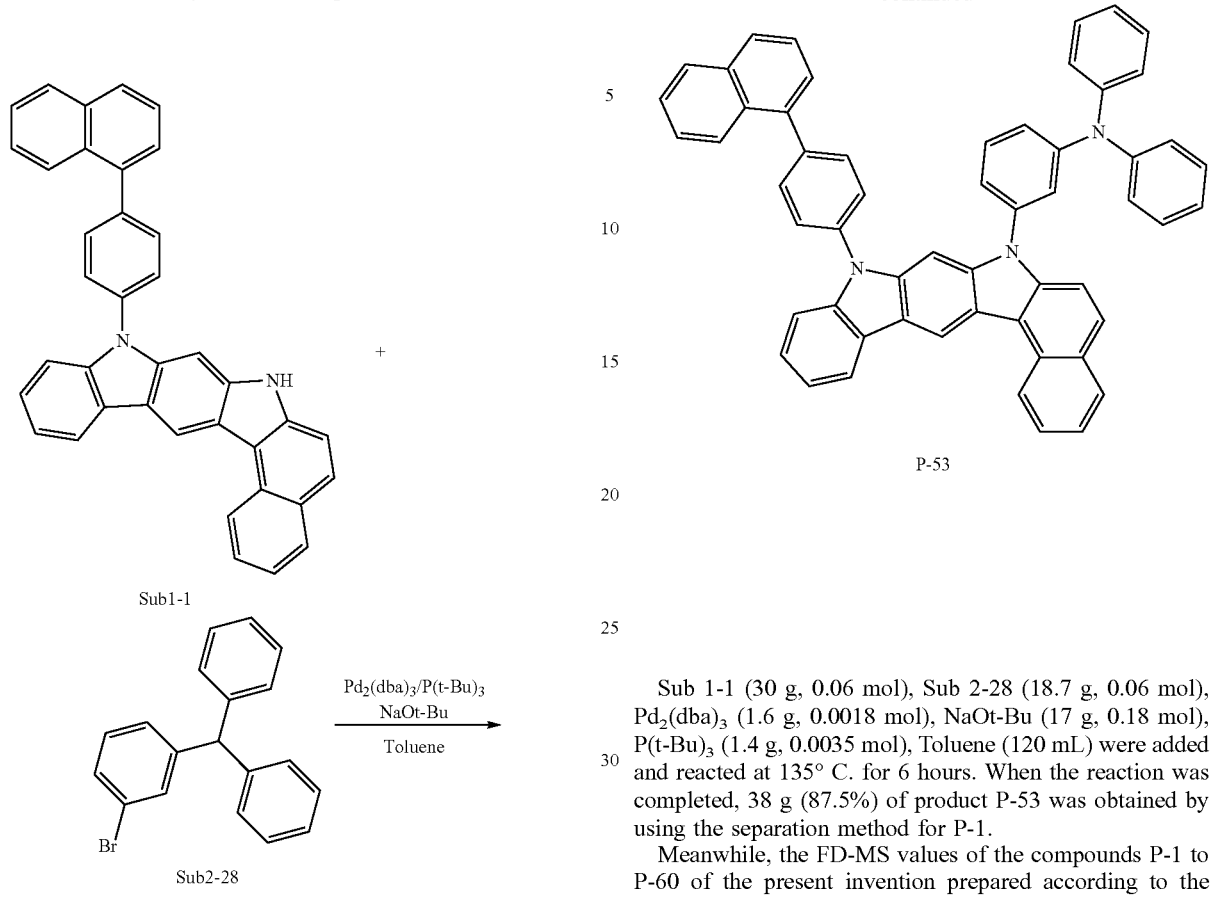

Sub 1-1 (30 g, 0.06 mol), Sub 2-28 (18.7 g, 0.06 mol), Pd$_2$(dba)$_3$ (1.6 g, 0.0018 mol), NaOt-Bu (17 g, 0.18 mol), P(t-Bu)$_3$ (1.4 g, 0.0035 mol), Toluene (120 mL) were added and reacted at 135° C. for 6 hours. When the reaction was completed, 38 g (87.5%) of product P-53 was obtained by using the separation method for P-1.

Meanwhile, the FD-MS values of the compounds P-1 to P-60 of the present invention prepared according to the above synthesis examples are shown in Table 3 below.

TABLE 3

| compound | FD-MS | compound | FD-MS |
|---|---|---|---|
| P-1 | m/z = 584.23(C$_{44}$H$_{28}$N$_2$ = 584.72) | P-2 | m/z = 634.24(C$_{48}$H$_{30}$N$_2$ = 634.78) |
| P-3 | m/z = 634.24(C$_{48}$H$_{30}$N$_2$ = 634.78) | P-4 | m/z = 660.26(C$_{50}$H$_{33}$N$_2$ = 660.82) |
| P-5 | m/z = 660.26(C$_{50}$H$_{32}$N$_2$ = 660.82) | P-6 | m/z = 660.26(C$_{50}$H$_{32}$N$_2$ = 660.82) |
| P-7 | m/z = 736.29(C$_{56}$H$_{36}$N$_2$ = 736.92) | P-8 | m/z = 736.29(C$_{56}$H$_{36}$N$_2$ = 736.92) |
| P-9 | m/z = 736.29(C$_{56}$H$_{36}$N$_2$ = 736.92) | P-10 | m/z = 736.29(C$_{56}$H$_{36}$N$_2$ = 736.92) |
| P-11 | m/z = 736.29(C$_{56}$H$_{36}$N$_2$ = 736.92) | P-12 | m/z = 684.26(C$_{52}$H$_{32}$N$_2$ = 684.84) |
| P-13 | m/z = 684.26(C$_{52}$H$_{32}$N$_2$ = 684.84) | P-14 | m/z = 734.27(C$_{56}$H$_{34}$N$_2$ = 734.9) |
| P-15 | m/z = 690.21(C$_{50}$H$_{30}$N$_2$S = 690.86) | P-16 | m/z = 674.24(C$_{50}$H$_{30}$N$_2$O = 674.8) |
| P-17 | m/z = 750.27(C$_{56}$H$_{34}$N$_2$O = 750.9) | P-18 | m/z = 749.28(C$_{56}$H$_{35}$N$_3$ = 749.92) |
| P-19 | m/z = 700.29(C$_{53}$H$_{36}$N$_2$ = 700.89) | P-20 | m/z = 690.21(C$_{50}$H$_{30}$N$_2$S = 690.86) |
| P-21 | m/z = 750.27(C$_{56}$H$_{34}$N$_2$O = 750.9) | P-22 | m/z = 749.28(C$_{56}$H$_{35}$N$_3$ = 749.92) |
| P-23 | m/z = 816.26(C$_{60}$H$_{36}$N$_2$S = 817.02) | P-24 | m/z = 740.23(C$_{54}$H$_{32}$N$_2$S = 740.92) |
| P-25 | m/z = 588.25(C$_{44}$H$_{24}$D$_4$N$_2$ = 588.75) | P-26 | m/z = 638.27(C$_{48}$H$_{26}$D$_4$N$_2$ = 638.81) |
| P-27 | m/z = 638.27(C$_{48}$H$_{26}$D$_4$N$_2$ = 638.81) | P-28 | m/z = 664.28(C$_{50}$H$_{28}$D$_4$N$_2$ = 664.84) |
| P-29 | m/z = 668.31(C$_{50}$H$_{24}$D$_8$N$_2$ = 668.87) | P-30 | m/z = 661.26(C$_{50}$H$_{31}$DN$_2$ = 661.83) |
| P-31 | m/z = 744.34(C$_{56}$H$_{28}$D$_8$N$_2$ = 744.97) | P-32 | m/z = 740.31(C$_{56}$H$_{32}$D$_4$N$_2$ = 740.94) |
| P-33 | m/z = 736.29(C$_{56}$H$_{36}$N$_2$ = 736.92) | P-34 | m/z = 736.29(C$_{56}$H$_{36}$N$_2$ = 736.92) |
| P-35 | m/z = 760.29(C$_{58}$H$_{36}$N$_2$ = 760.94) | P-36 | m/z = 684.26(C$_{52}$H$_{32}$N$_2$ = 684.84) |
| P-37 | m/z = 734.27(C$_{56}$H$_{34}$N$_2$ = 734.9) | P-38 | m/z = 738.3(C$_{56}$H$_{30}$D$_4$N$_2$ = 738.93) |
| P-39 | m/z = 790.24(C$_{58}$H$_{34}$N$_2$S = 790.98) | P-40 | m/z = 837.37(C$_{62}$H$_{27}$D$_{11}$N$_2$O = 838.07) |
| P-41 | m/z = 750.27(C$_{56}$H$_{34}$N$_2$O = 750.9) | P-42 | m/z = 595.29(C$_{44}$H$_{17}$D$_{11}$N$_2$ = 595.79) |
| P-43 | m/z = 700.29(C$_{53}$H$_{36}$N$_2$ = 700.89) | P-44 | m/z = 766.24(C$_{56}$H$_{34}$N$_2$S = 766.96) |
| P-45 | m/z = 734.31(C$_{54}$H$_{22}$D$_{10}$N$_2$O = 734.92) | P-46 | m/z = 774.29(C$_{56}$H$_{26}$D$_8$N$_2$S = 775.01) |
| P-47 | m/z = 724.25(C$_{54}$H$_{32}$N$_2$O = 724.86) | P-48 | m/z = 742.24(C$_{54}$H$_{30}$D$_2$N$_2$S = 742.94) |
| P-49 | m/z = 710.27(C$_{54}$H$_{34}$N$_2$ = 710.88) | P-50 | m/z = 710.27(C$_{54}$H$_{34}$N$_2$ = 710.88) |
| P-51 | m/z = 766.24(C$_{56}$H$_{34}$N$_2$S = 766.96) | P-52 | m/z = 760.29(C$_{58}$H$_{36}$N$_2$ = 760.94) |
| P-53 | m/z = 751.3(C$_{56}$H$_{37}$N$_3$ = 751.93) | P-54 | m/z = 642.3(C$_{48}$H$_{34}$D$_2$N$_2$ = 642.84) |
| P-55 | m/z = 754.29(C$_{56}$H$_{30}$D$_4$N$_2$O = 754.93) | P-56 | m/z = 735.32(C$_{54}$H$_{21}$D$_{11}$N$_2$O = 735.93) |
| P-57 | m/z = 841.31(C$_{62}$H$_{39}$N$_3$O = 842.01) | P-58 | m/z = 621.31(C$_{46}$H$_{23}$D$_9$N$_2$ = 621.83) |
| P-59 | m/z = 598.31(C$_{44}$H$_{14}$D$_{14}$N$_2$ = 598.81) | P-60 | m/z = 712.28(C$_{54}$H$_{32}$D$_2$N$_2$ = 712.89) |

In the present invention, Avg. $\Delta E_{st}$ can be expressed as Avg. S1-T1, and means the average value of the difference between the singlet energy (S1) and the triplet energy (T1) of a specific single molecule in a different molecule in a mixed state of different compounds. For smooth calculation, a triazine-based compound was used as a compound showing electrical properties among different compounds, and other compounds utilized the compounds of the present invention. In more detail, as the triazine-based compound, a triazine-based compound composed of a $C_6$-$C_{20}$ aryl group or a triazine-based compound in which a heterocyclic ring containing O, S, Si or N elements is substituted was used, and the $\Delta E_{st}$ value was measured in a state in which the triazine-based compound and the compound of the present invention were mixed.

In more detail about Avg. $\Delta E_{st}$, a number of electron donor and acceptor monomolecules [128] are placed in a constant ratio [P:N=5:5] in a unit cell with a periodic boundary condition (PBC), and for this molecular dynamics simulation is performed. Molecular dynamics simulation was performed in a total of 4 steps, and the first step was conducted at a temperature of 10 Kelvin (K) under the condition of a constant volume according to Brownian mechanics. The second step also proceeds according to Brownian dynamics, but proceeds at a temperature of 100 Kelvin (K) under constant atmospheric pressure (1.01325 bar). Then, in the third step, molecular dynamics according to the force field is calculated, and the process proceeds by 0.1 nanoseconds (ns) at a constant pressure (atmospheric pressure) and temperature (room temperature). Finally, under the same conditions as in the third step (atmospheric pressure, room temperature), the molecular dynamics process is performed in units of 2 femtoseconds (fs), and the simulation is performed until a predetermined time [140 nanoseconds] is required. At this time, the predetermined time should be long enough so that the amorphous solid structure can reach the equilibrium state. After that, structural data at the final time point [140 nanoseconds] are extracted, and dimers with different monomer (donor and acceptor) are extracted (sampled) from the corresponding structure. In this case, the conditions for extracting dimers were when the distance between heterodimers was less than 2.4 Å, and some [⅓] of dimers that met the conditions were randomly selected and used for calculation. For dimers extracted through quantum mechanics simulation, single-point energy calculation is performed through time dependent density functional theory (TD-DFT), therefore the first lowest singlet excitation energy (S1) and the first lowest triplet excitation energy (T1) of each heterodimers are calculated. At this time, the difference between S1 and T1 is called the first singlet-triplet excitation energy ($\Delta$Est) difference of the heterodimer.

All calculations were made through molecular simulation (Schrodinger Materials Science Suite 4.1.161), and the Desmond package was used for molecular dynamics simulation. Molecular dynamics simulations were conducted under the NPT ensemble using the Nose-Hoover chain method and the Martyna-Tobias-Klein method. Quantum chemical properties based on the first principle were calculated by extracting monomers from the structure obtained through molecular dynamics simulation, and Gaussian and Jaguar packages were used in this process. In quantum mechanics calculations through Jaguar, first singlet/triplet excitation energies were calculated using TD-DFT, and the calculation method (Method/Basis set) was performed with the commonly used B3LYP/6-31G.

A heterodimer as defined in the present invention is two different molecules having a molecular dynamically determined dimer conformation, and at this time, the two molecules correspond to molecules functioning as P-type and N-type (hole, electron) host materials, respectively, and the minimum distance between molecules must be 2.4 Å or less. In order to find these heterodimers, a multimolecular structure in which two molecules are mixed in a ratio of P:N=4:6 is created, and molecular dynamics simulation proceeds in several steps to find the most stable molecular dynamics (equilibrium point). At this time, the conformation of the molecule has a modified form from the quantum-mechanically optimized structure of a general single molecule (gas phase state) due to intermolecular interaction, and accordingly, the shape and properties of the molecules have a distribution that does not have a constant value, and exhibit characteristics different from those of a monomolecular structure (gas-phase molecule).

Exciplex is a special kind of heterodimer and means an excited heterodimer.

To check the excited state of the heterodimer determined molecular dynamics, extract the heterodimer below a certain minimum distance between molecules and, for this, calculate the excited state based on the time-dependent density functional theory (TD-DFT). At this time, the single point energy is calculated to irradiate the exciplex on the solid phase, and this result corresponds to the vertical excitation energy according to the excited state (singlet, triplet) of the solid-phase heterodimer.

To determine whether exciplex is formed, heterodimers were separated, and singlet excitation energy was calculated for each single molecule by single-point energy calculation according to the density functional theory, and the following discriminant was determined according to the literature.

$$\min(S_1^P, S_1^N) - S_1^{P-N\ complex} \geq 0.15\ eV$$

In this data, only heterodimers that meet the above conditions were used for calculation, and this is defined as exciplex in the solid phase.

$\Delta E_{st}$ values measured based on this are shown in Table 4 below.

TABLE 4

| compound | $\Delta E_{st}$ |
| --- | --- |
| P-1 | 0.2094 |
| P-25 | 0.1997 |
| P-42 | 0.2035 |
| comparative compound A | 0.2591 |
| comparative compound B | 0.3082 |
| comparative compound C | 0.2185 |
| comparative compound D | 0.2212 |
| comparative compound E | 0.2128 |
| comparative compound F | 0.2466 |

[Example 1]: Red Organic Light Emitting Device (Phosphorescent Host)

An organic electroluminescent device was manufactured according to a conventional method by using the compound obtained through synthesis as a light emitting host material of the emitting layer. First, a N1-(naphthalen-2-yl)-N4,N4-bis(4-(naphthalen-2-yl(phenyl)amino)phenyl)-N1-phenylbenzene-1,4-diamine (abbreviated as 2-TNATA) film was vacuum-deposited on the ITO layer (anode) formed on a glass substrate to form a 60 nm-thick hole injection layer, and 4,4-bis[N-(1-naphthyl)-N-phenylamino]biphenyl (hereinafter abbreviated as —NPD) as a hole transport compound on the hole injection layer was vacuum-deposited to a thickness of 60 nm to form a hole transport layer.

As a host on the hole transport layer, the compound (P-1) of the present invention represented by Formula (1) and DSNL1 were used in a weight ratio (5:5), and (piq)$_2$Ir(acac) [bis-(1-phenylisoquinolyl)iridium(III)acetylacetonate] as a dopant material was doped at a weight ratio of 95:5 to deposit an emitting layer to a thickness of 30 nm). Subsequently, (1,1'-bisphenyl)-4-oleato)bis(2-methyl-8-quinolineoleato)aluminum (abbreviated as BAlq) as a hole-blocking layer was vacuum-deposited to a thickness of 10 nm, and as an electron transport layer, tris(8-quinolinol)aluminum (abbreviated as Alq3) was deposited to a thickness of 40 nm. Then, as an electron injection layer, LiF, an alkali metal halide, was deposited to a thickness of 0.2 nm, and then, Al was deposited to a thickness of 150 nm and used as a cathode to prepare an organic electroluminescent device.

<DSNL1>

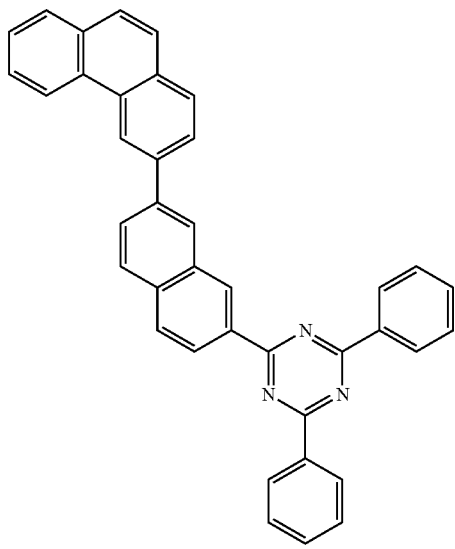

<DSNL2>

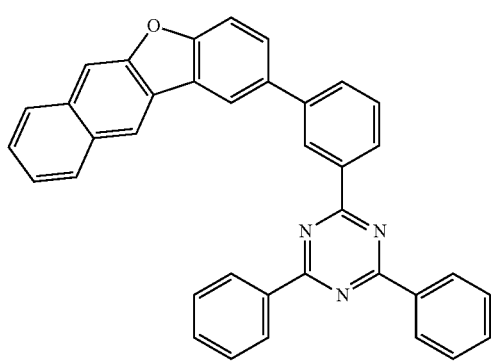

[Example 2] to [Example 14]

An organic electroluminescent device was prepared in the same manner as in Example 1, except that the compound DSNL1 or DSNL2 and the compound of the present invention described in Table 5 were used instead of the compound (P-1) of the present invention as the host material of the emitting layer.

[Comparative Example 1] to [Comparative Example 12]

An organic electroluminescent device was prepared in the same manner as in Example 1, except that the compound DSNL1 or DSNL2 and Comparative Compound A to Comparative Compound F were used as the host material of the emitting layer.

<Comparative Compounds A, B and C>

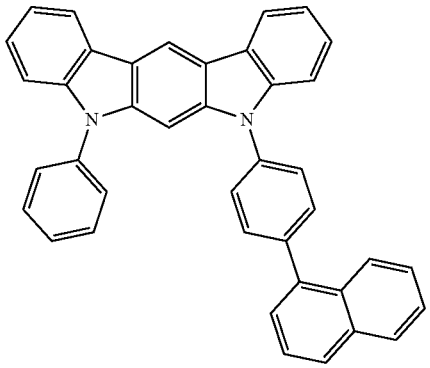

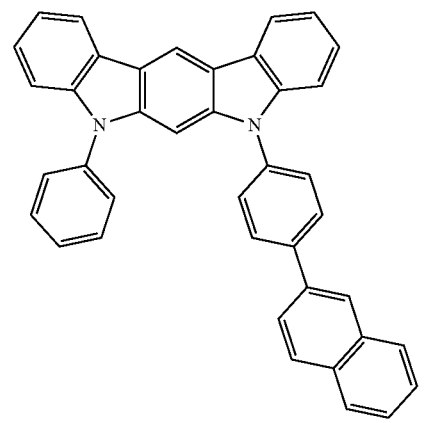

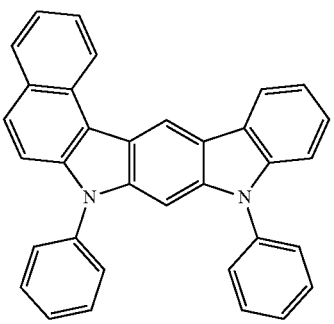

<Comparative Compounds D, E and F>

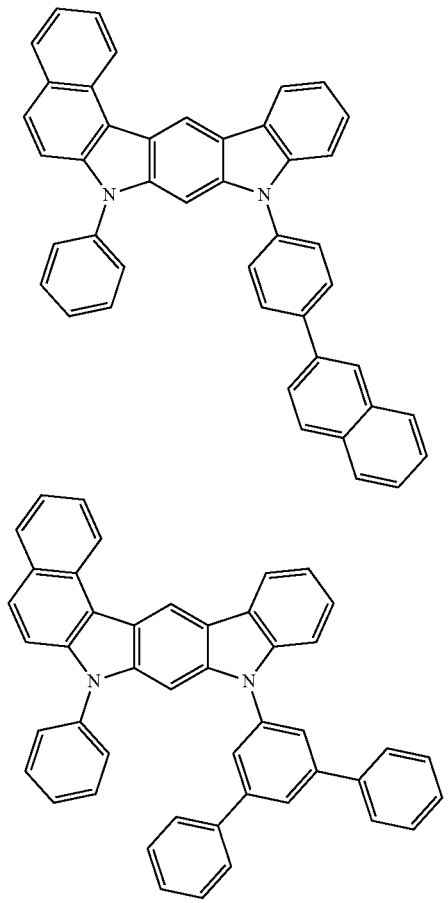

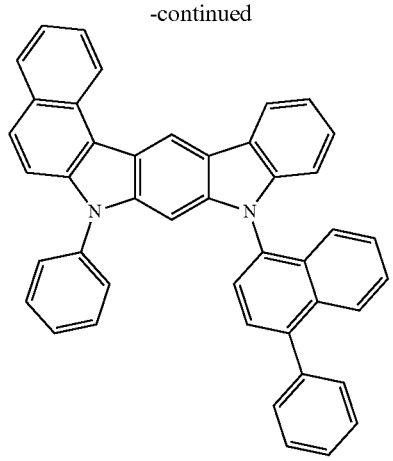

By applying a forward bias DC voltage to the organic electronic devices prepared in Examples 1 to 14 and Comparative Examples 1 to 12 prepared in this way, Electroluminescence (EL) characteristics were measured with PR-650 from photo research, and as a result of the measurement, the T95 lifetime was measured using a lifetime measuring device manufactured by McScience at 2500 cd/m² standard luminance. Table 5 below shows the device fabrication and evaluation results.

TABLE 5

| | First compound | Second compound | Voltage (v) | Current Density (mA/cm²) | Brightness (cd/m²) | Efficiency (cd/A) | T(95) |
|---|---|---|---|---|---|---|---|
| comparative example(1) | DSNL1 | comparative compound A | 5.3 | 15.8 | 2500 | 15.8 | 109.8 |
| comparative example(2) | | comparative compound B | 5.3 | 16.0 | 2500 | 15.6 | 108.0 |
| comparative example(3) | | comparative compound C | 5.0 | 14.0 | 2500 | 17.8 | 113.7 |
| comparative example(4) | | comparative compound D | 5.0 | 15.5 | 2500 | 16.1 | 112.5 |
| comparative example(5) | | comparative compound E | 5.1 | 14.5 | 2500 | 17.2 | 115.4 |
| comparative example(6) | | comparative compound F | 4.9 | 12.6 | 2500 | 19.8 | 110.3 |
| comparative example(7) | DSNL2 | comparative compound A | 5.2 | 16.6 | 2500 | 15.1 | 107.8 |
| comparative example(8) | | comparative compound B | 5.2 | 16.8 | 2500 | 14.9 | 106.4 |
| comparative example(9) | | comparative compound C | 4.9 | 15.2 | 2500 | 16.5 | 111.5 |
| comparative example(10) | | comparative compound D | 4.9 | 15.9 | 2500 | 15.7 | 110.7 |
| comparative example(11) | | comparative compound E | 4.9 | 15.4 | 2500 | 16.2 | 113.1 |
| comparative example(12) | | comparative compound F | 4.8 | 13.6 | 2500 | 18.4 | 108.2 |
| example(1) | DSNL1 | P-1 | 4.6 | 8.0 | 2500 | 31.2 | 138.40 |
| example(2) | | P-4 | 4.6 | 8.8 | 2500 | 28.4 | 136.60 |
| example(3) | | P-16 | 4.5 | 10.7 | 2500 | 23.3 | 132.70 |

TABLE 5-continued

| | First compound | Second compound | Voltage (v) | Current Density (mA/cm$^2$) | Brightness (cd/m$^2$) | Efficiency (cd/A) | T(95) |
|---|---|---|---|---|---|---|---|
| example(4) | | P-19 | 4.7 | 9.5 | 2500 | 26.3 | 129.80 |
| example(5) | | P-25 | 4.6 | 8.1 | 2500 | 30.8 | 149.50 |
| example(6) | | P-42 | 4.6 | 9.0 | 2500 | 27.9 | 147.10 |
| example(7) | | P-46 | 4.5 | 10.1 | 2500 | 24.8 | 130.40 |
| example(8) | DSNL2 | P-1 | 4.5 | 8.1 | 2500 | 30.7 | 132.4 |
| example(9) | | P-4 | 4.4 | 9.5 | 2500 | 26.2 | 130.7 |
| example(10) | | P-16 | 4.3 | 11.3 | 2500 | 22.2 | 127.5 |
| example(11) | | P-19 | 4.6 | 10.2 | 2500 | 24.6 | 122.4 |
| example(12) | | P-25 | 4.5 | 8.8 | 2500 | 28.3 | 137.2 |
| example(13) | | P-42 | 4.6 | 9.7 | 2500 | 25.8 | 136.6 |
| example(14) | | P-46 | 4.4 | 10.6 | 2500 | 23.5 | 125.7 |

As can be seen from the results in Table 5, when the compound of the present invention is used as a material for the emitting layer, it can be seen that the driving voltage is lowered and the efficiency and lifespan are significantly improved compared to the case of using the comparative compounds A to F.

More specifically, the compound of the present invention has a lower $\Delta E_{st}$ value than the comparative compound. This $\Delta E_{st}$ value is largely determined according to the composition of the substituents substituted in the structure serving as the mother structure. Depending on the substitution of a specific substituent, the $\Delta E_{st}$ value is a section showing a very small difference between 0.210 or less and a value higher than 0.210, but shows a significant difference in lifespan starting from the value of 0.210. In the present invention, it was confirmed that the substituent determining the low $\Delta E_{st}$ value had a structure in which naphthyl was substituted for phenyl, and furthermore, it was confirmed that when deuterium was substituted for phenyl and naphthyl, it had a lower $\Delta E_{st}$ value. Looking at the relationship between these $\Delta E_{st}$ values and the device results, in general, exciplex has a lower S1-T1 ($\Delta E_{st}$) energy difference compared to single molecules, which lowers the exciton binding energy (binding energy between electrons and holes) in the triplet state. Accordingly, when excitons are formed, surplus energy is reduced, and thermal energy emitted due to non-radiative decay of excitons is also reduced. Since these extra energies generated in the light emitting process cause damage to the OLED device, forming an exciplex in the emitting layer is advantageous in terms of the lifetime of the device.

The S1-T1 energy difference ($\Delta E_{st}$) of each exciplex is used to compare the effect of exciplex on lifespan.

$$\Delta E_{st} = \Delta (S_1^{exciplex} - T_1^{exciplex})$$

The smaller the S1-T1 energy difference of the exciplex, the smaller the orbital overlap matrix element between the two molecules, and thus the fluorescence lifespan is increased. Exciplex in the fluorescence state (S1) transmits energy to the dopant, but if it is not delivered and its lifespan is over, it is dissipated as thermal energy through the non-luminescent path, causing thermal degradation in the device. Therefore, as the fluorescence lifetime of Exciplex having a low S1-T1 energy difference increases, the energy transfer efficiency to the light emitting body increases, which improves the device lifespan by reducing the thermal performance degradation caused by the non-luminous path.

In the present invention, it was confirmed that it has a low $\Delta E_{st}$ value as a specific substituent is substituted, and when deuterium was substituted at a specific position, it had a lower $\Delta E_{st}$ value. Based on this, the molecular structure was designed and the device was measured. As a result, excellent device results such as those described above can be confirmed.

Comparing the compounds of the present invention, it can be seen that the lifespan is reduced in the case of a substituent containing a chemically unstable element, and the driving voltage and efficiency could be determined according to the overall HOD (hole only device) and EOD (electron only device) values. It can be seen that in the case of such HOD and EOD, it is determined depending on the form or energy level of the plate-like structure of the compound. As a result, the mobility of holes and electrons is determined according to the type of substituents substituted in the same skeleton, and the compound of the embodiment shows different characteristics according to the different mobility.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:
1. A compound of Formula (1):

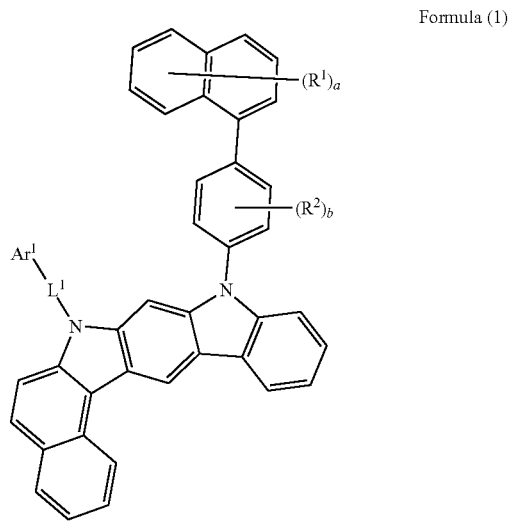

Formula (1)

wherein:
1) Ar$^1$ is selected from the group consisting of a C$_6$-C$_{60}$ aryl group; a fluorenyl group; a C$_2$-C$_{60}$ heterocyclic group including at least one heteroatom of O, N, S, Si or P; -L'-NR$^a$R$^b$,
2) L$^1$ and L' are each independently selected from the group consisting of a single bond; a C$_6$-C$_{60}$ arylene group; and a C$_2$-C$_{60}$ heterocyclic group including at least one heteroatom of O, N, S, Si or P,
3) R$^a$ and R$^b$ are each independently selected from the group consisting of a C$_6$-C$_{60}$ aryl group; a fluorenyl group; a fused ring group of a C$_3$-C$_{60}$ aliphatic ring and a C$_6$-C$_{60}$ aromatic ring; a C$_2$-C$_{60}$ heterocyclic group including at least one heteroatom of O, N, S, Si or P, an C$_1$~C$_{50}$ alkyl group, an C$_2$~C$_{20}$ alkenyl group, a C$_2$-C$_{20}$ alkynyl group, a C$_1$-C$_{30}$ alkoxy group, and a C$_6$-C$_{30}$ aryloxy group,
4) R$^1$ and R$^2$ are deuterium,
5) a is an integer from 0 to 7, b is an integer from 0 to 4,
wherein, the aryl group, arylene group, heterocyclic group, fluorenyl group, fused ring group, alkyl group, alkenyl group, alkynyl group, alkoxyl group and aryloxy group may be substituted with one or more substituents selected from the group consisting of deuterium; halogen; silane group; siloxane group; boron group; germanium group; cyano group; nitro group; C$_1$-C$_{20}$ alkylthio group; C$_1$-C$_{20}$ alkoxy group; C$_1$-C$_{20}$ alkyl group; C$_2$-C$_{20}$ alkenyl group; C$_2$-C$_{20}$ alkynyl group; C$_6$-C$_{20}$ aryl group; C$_6$-C$_{20}$ aryl group substituted with deuterium; a fluorenyl group; C$_2$~C$_{20}$ heterocyclic group; C$_3$-C$_{20}$ cycloalkyl group; C$_7$-C$_{20}$ arylalkyl group; C$_8$-C$_{20}$ arylalkenyl group; and -L'-NR$^a$R$^b$; or the substituents may be bonded to each other to form a saturated or unsaturated ring, wherein the term 'ring' means a C$_3$-C$_{60}$ aliphatic ring or a C$_6$-C$_{60}$ aromatic ring or a C$_2$-C$_{60}$ heterocyclic group or a fused ring formed by the combination thereof.

2. The compound of claim 1, wherein the compound of Formula (1) is represented by a compound of Formula (1-1):

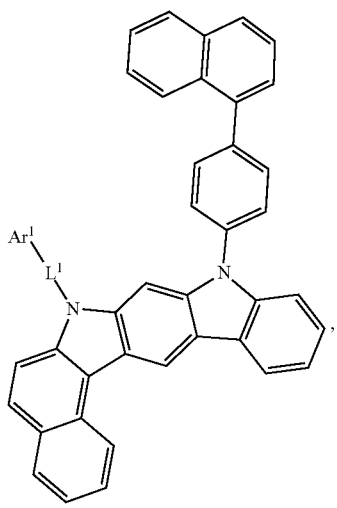

Formula (1-1)

wherein Ar$^1$ and L$^1$ are the same as defined in claim 1.

3. The compound of claim 1, wherein the compound of Formula (1) is represented by a compound of Formula (1-2):

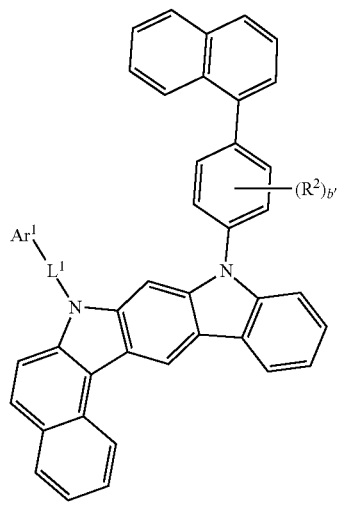

Formula (1-2)

wherein:
1) Ar$^1$, L$^1$ and R$^2$ are the same as defined in claim 1,
2) b' is an integer from 1 to 4.

4. The compound of claim 1, wherein the compound of Formula (1) is represented by a compound of Formula (1-3):

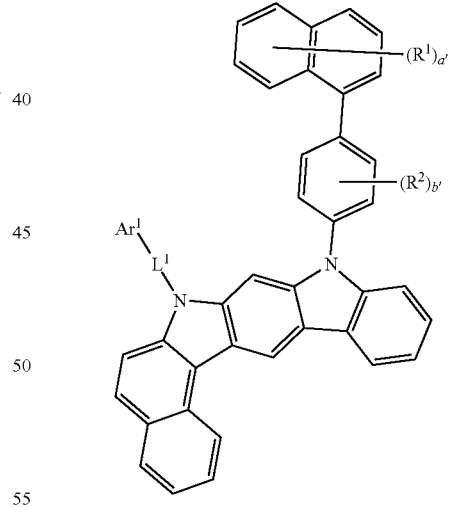

Formula (1-3)

wherein:
1) Ar$^1$, L$^1$, R$^1$ and R$^2$ are the same as defined in claim 1,
2) a' is an integer from 1 to 7, and b' is an integer from 1 to 4.

5. The compound of claim 1, wherein L$^1$ is a single bond or a C$_6$-C$_{60}$ arylene group, and Ar$^1$ is a C$_6$-C$_{18}$ aryl group.

6. The compound of claim 1, wherein the compound of Formula (1) is represented by a compound of Formula (2-1):

Formula (2-1)

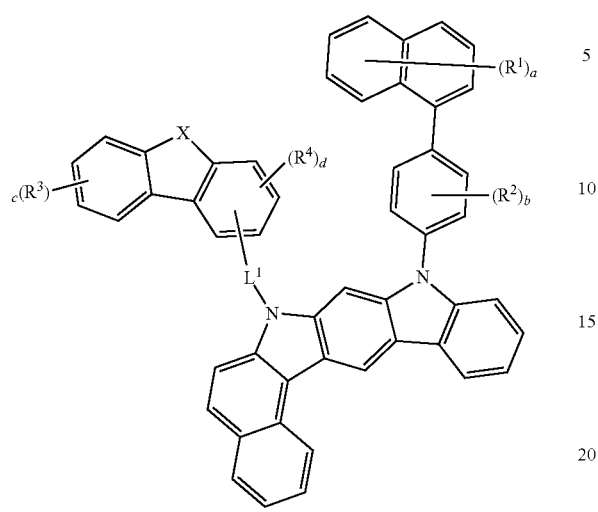

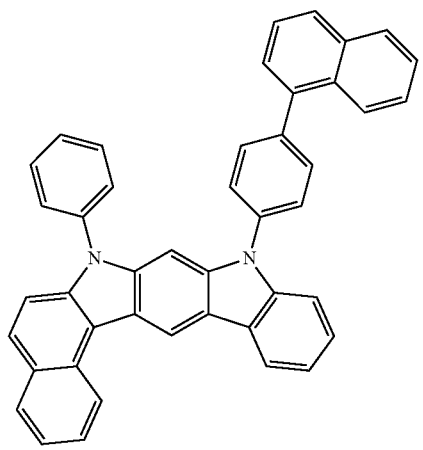
P-1 wherein:
1) X is O, S or NR$^c$,
2) R$^3$ and R$^4$ are each independently selected from the group consisting of hydrogen; a C$_6$-C$_{60}$ aryl group; a C$_2$-C$_{60}$ heterocyclic group including at least one heteroatom of O, N, S, Si or P; a fused ring group of a C$_3$-C$_{60}$ aliphatic ring and a C$_6$-C$_{60}$ aromatic ring; an C$_1$~C$_{50}$ alkyl group, an C$_2$~C$_{20}$ alkenyl group, a C$_2$-C$_{20}$ alkynyl group, a C$_1$-C$_{30}$ alkoxy group, and a C$_6$-C$_{30}$ aryloxy group, and -L'-NR$^a$R$^b$; or a plurality of adjacent R$^3$, or a plurality of R$^4$ may be bonded to each other to form a ring,
3) c is an integer of 0 to 4, d is an integer of 0 to 3,
4) L$^1$, R$^1$, R$^2$, a, b, L', R$^a$ and R$^b$ are the same as defined in claim 1, and
5) R$^c$ is selected from the group consisting of a hydrogen; a C$_6$-C$_{60}$ aryl group; a fluorenyl group; a C$_2$-C$_{60}$ heterocyclic group including at least one heteroatom of O, N, S, Si or P; a fused ring group of a C$_3$-C$_{60}$ aliphatic ring and a C$_6$-C$_{60}$ aromatic ring; an C$_1$-C$_{60}$ alkyl group, an C$_2$~C$_{20}$ alkenyl group, a C$_2$-C$_{20}$ alkynyl group, a C$_1$-C$_{30}$ alkoxy group, and a C$_6$-C$_{30}$ aryloxy group.

7. The compound of claim 1, wherein ΔE$_{st}$ value of the compound of Formula (1) is 0.2100 eV or less.

8. The compound of claim 1, wherein ΔE$_{st}$ value of the compound of Formula (1) is 0.150 to 0.2100 eV.

9. The compound of claim 1, wherein the compound of Formula (1) is selected from the group consisting of Compounds P-1 to P-60:

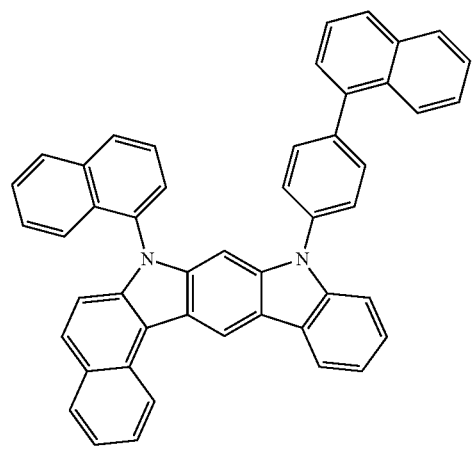
P-2

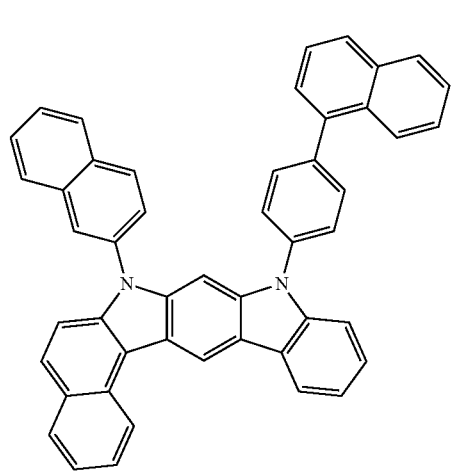
P-3

P-4
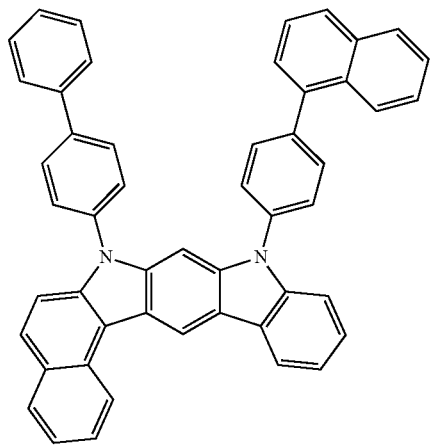
P-5
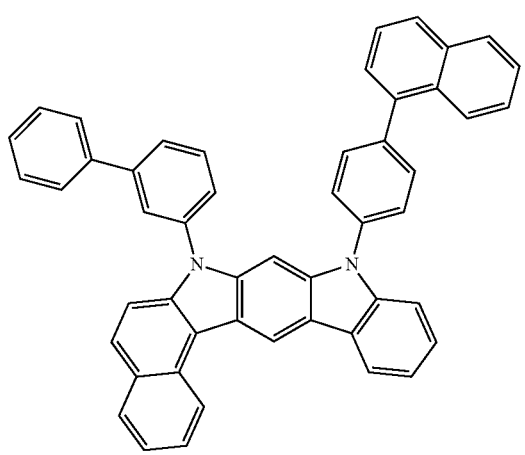
P-6
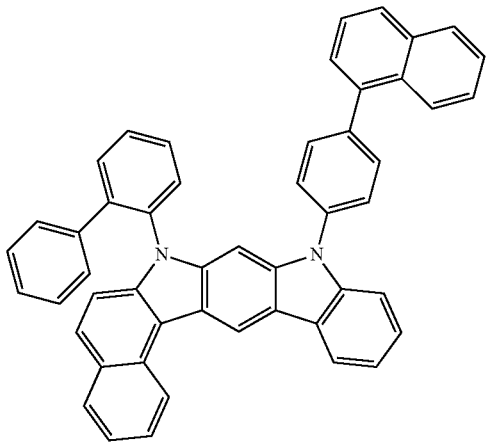
P-7
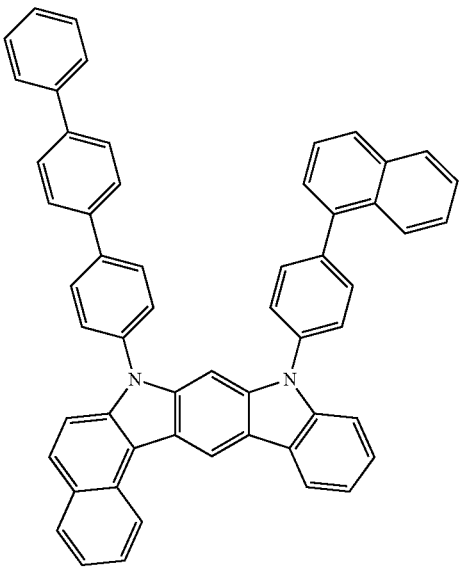
P-8
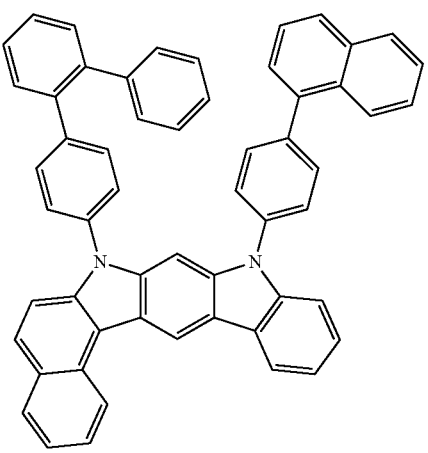
P-9
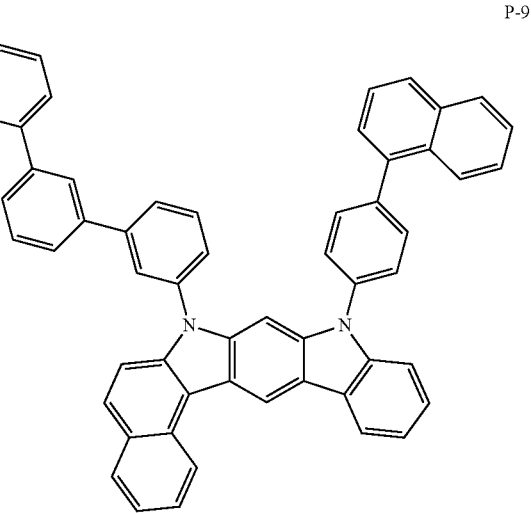

-continued
P-10
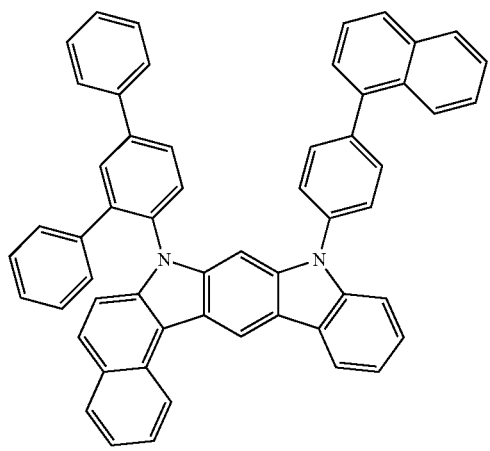
P-11
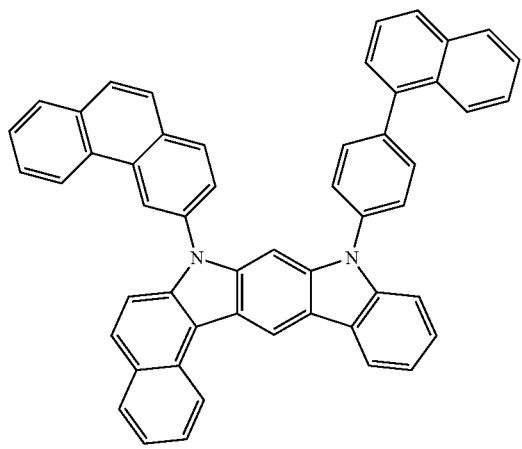
P-12
P-13
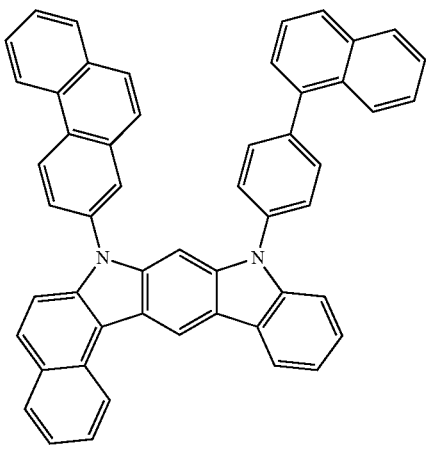
P-14
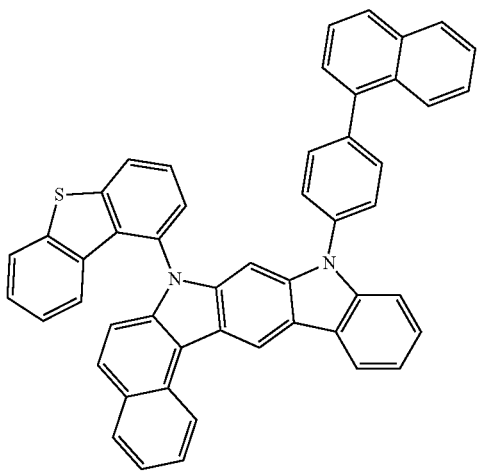
P-15

P-16
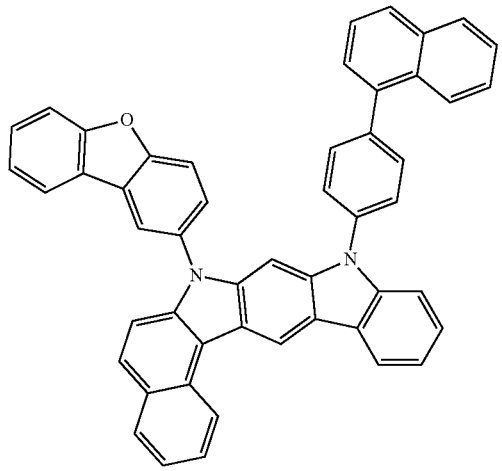
P-17
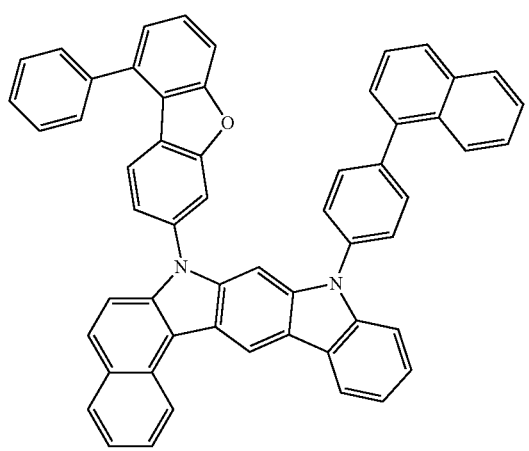
P-18
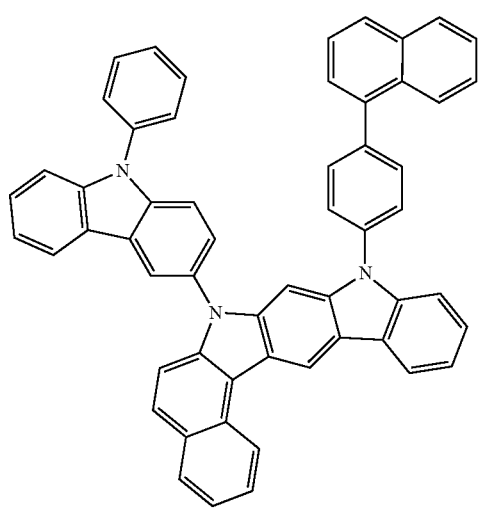
P-19
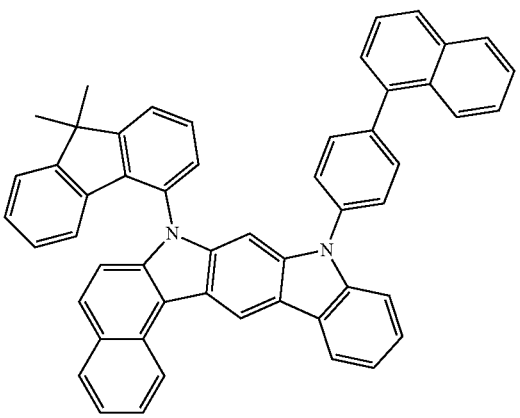
P-20
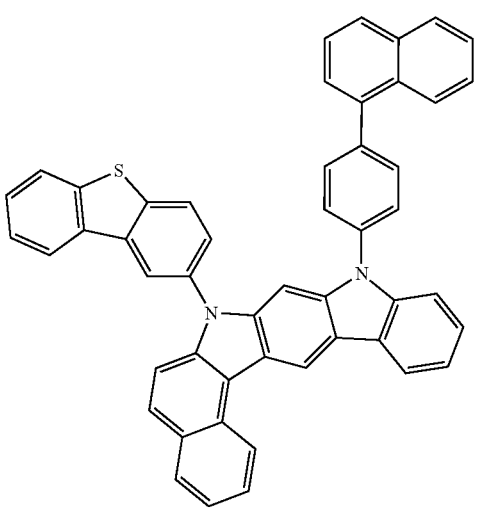
P-21
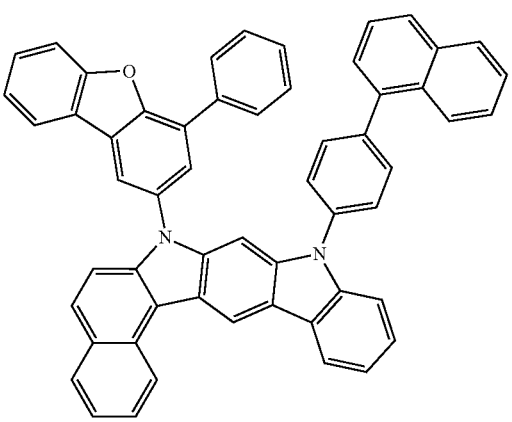

P-22
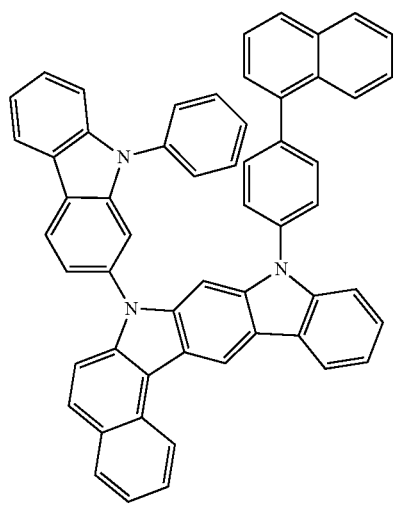
P-23
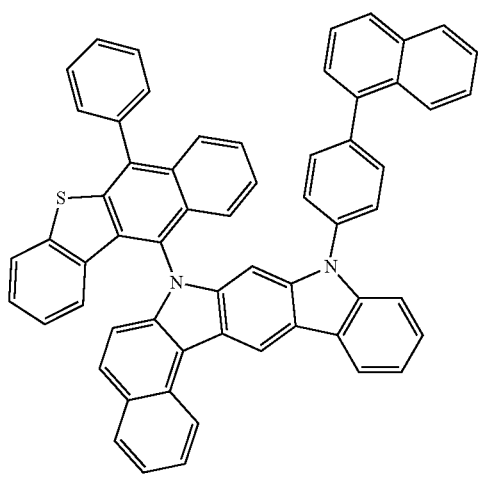
P-24
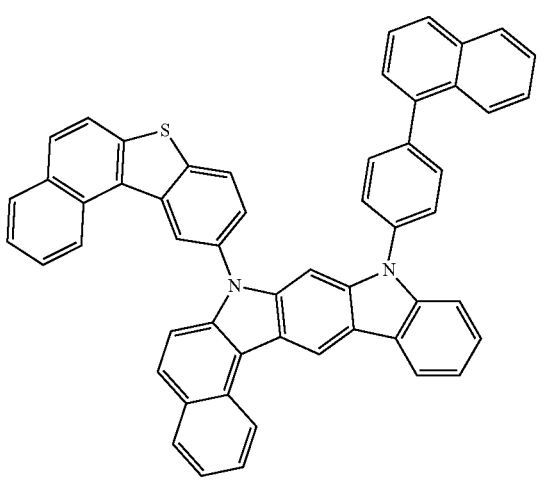
P-25
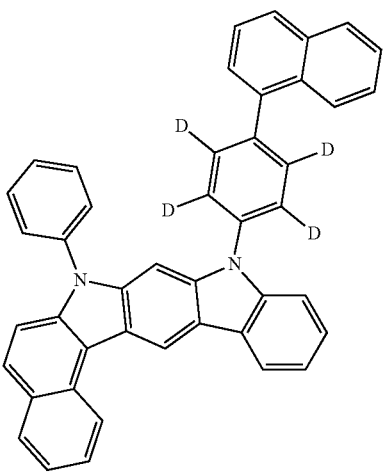
P-26
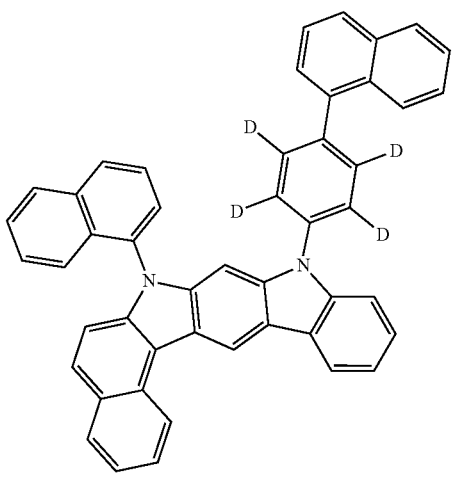
P-27
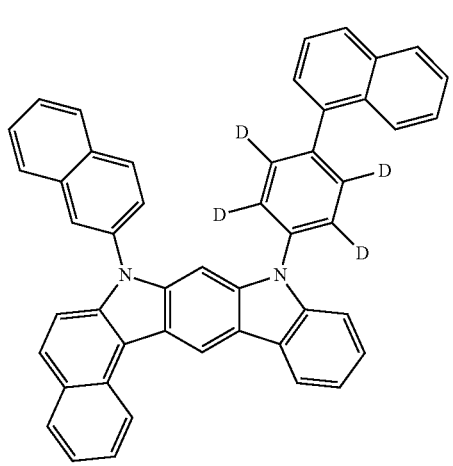

P-28
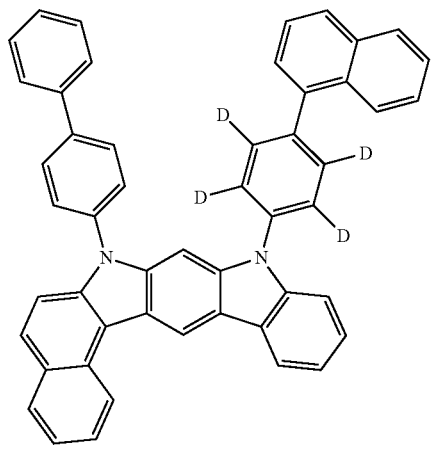
P-29
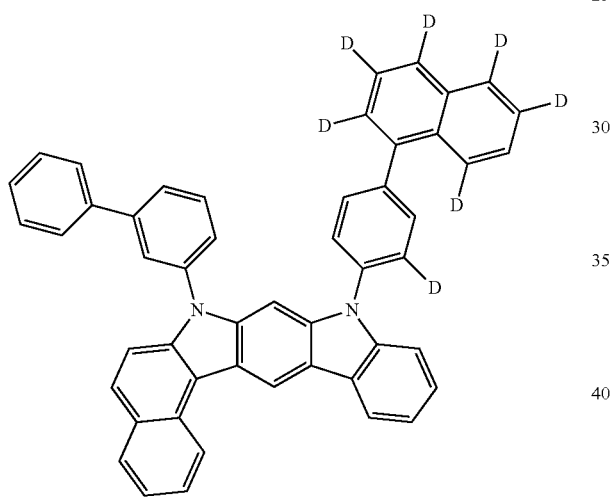
P-30
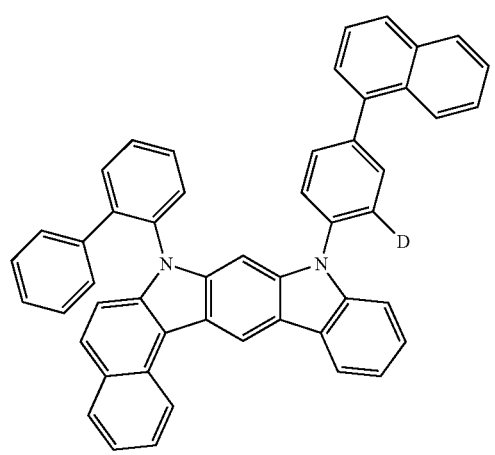
P-31
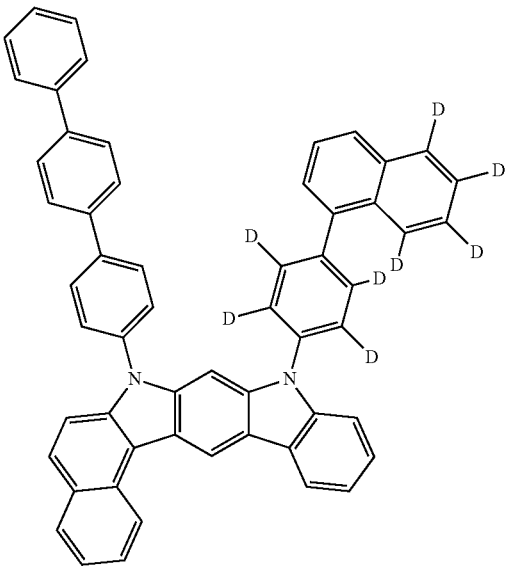
P-32
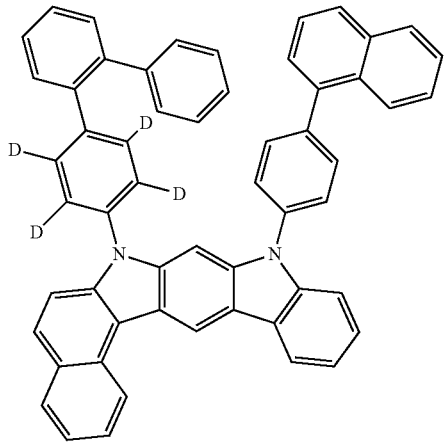
P-33
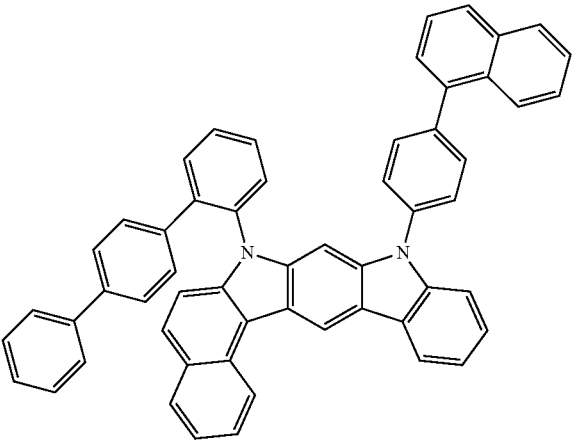

P-34
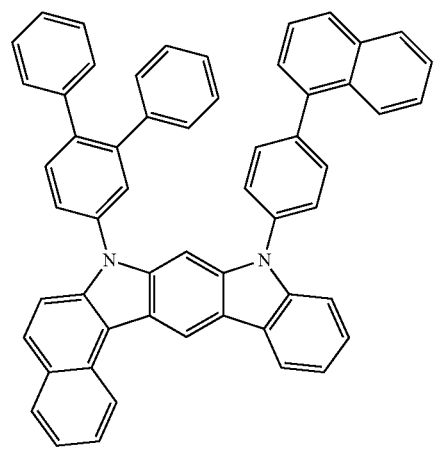
P-37
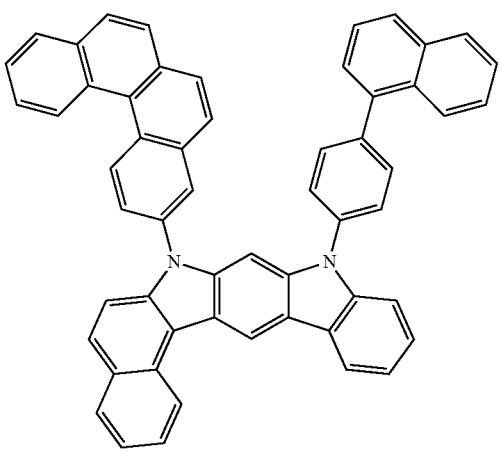
P-35
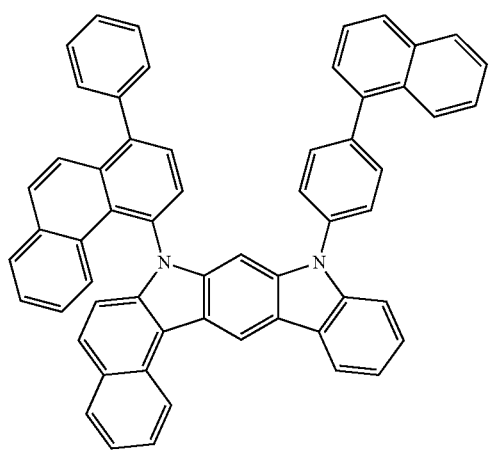
P-38
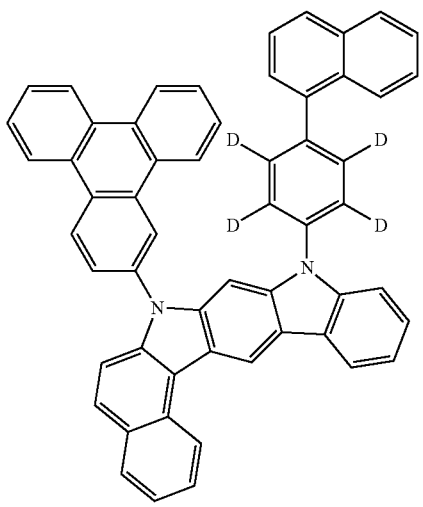
P-36
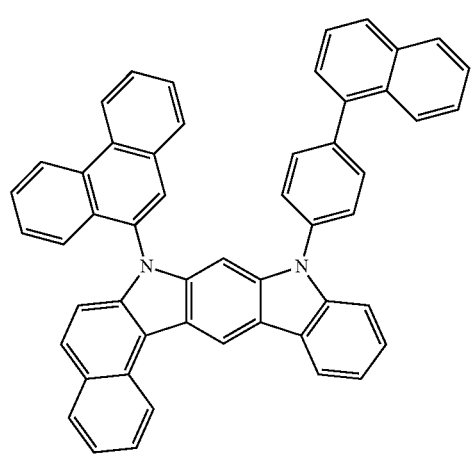
P-39
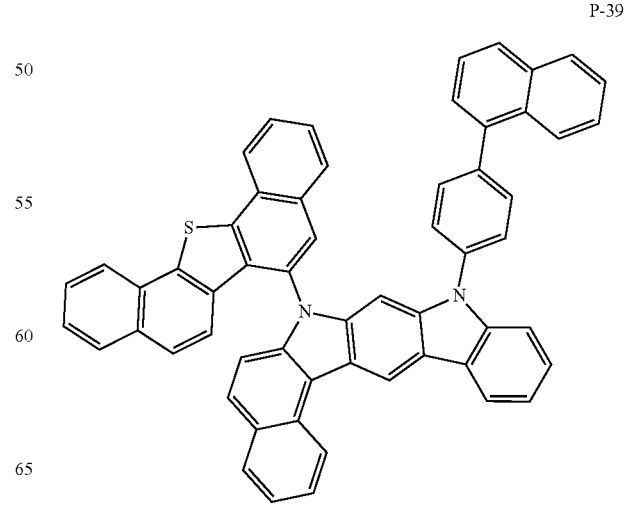

-continued
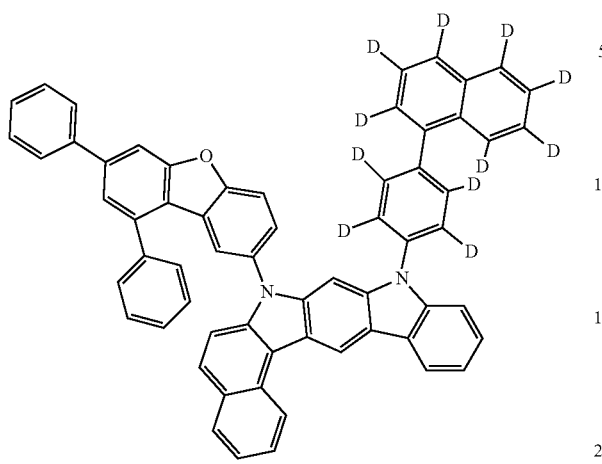
P-40
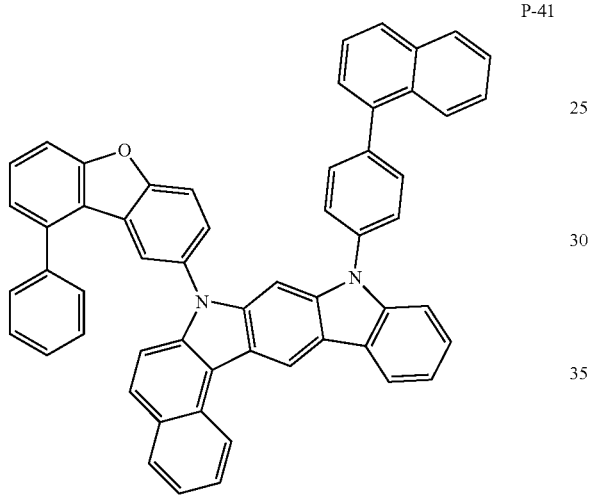
P-41
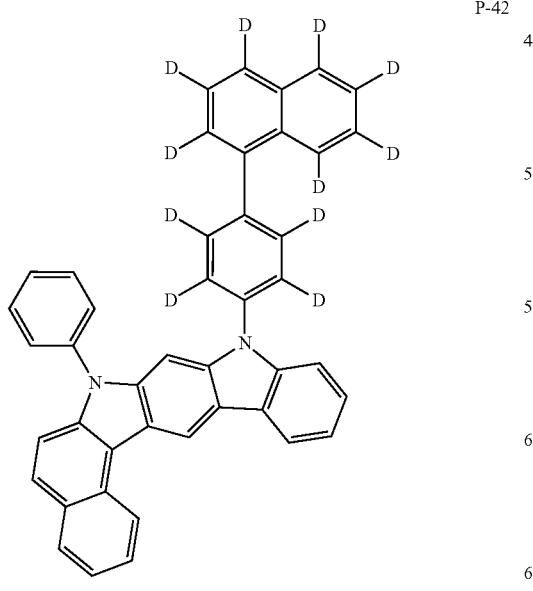
P-42
-continued
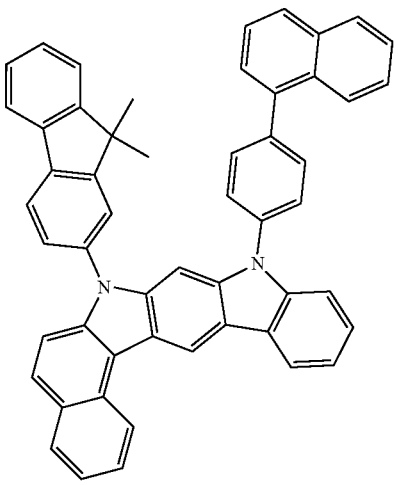
P-43
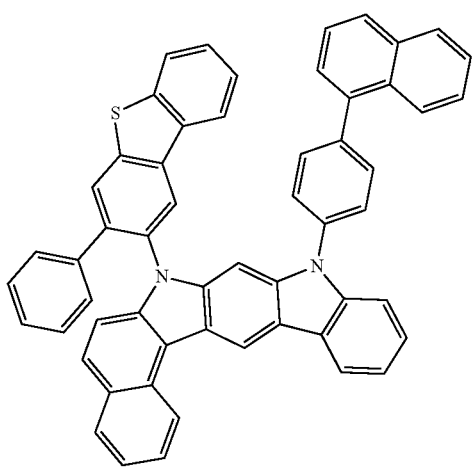
P-44
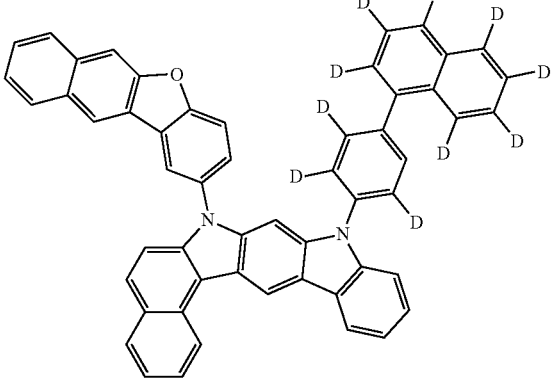
P-45

P-46
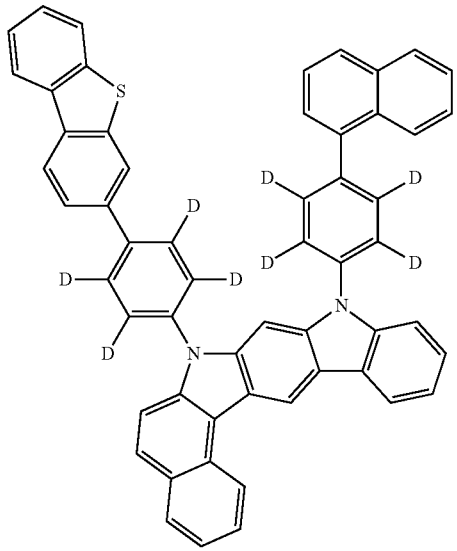
P-49
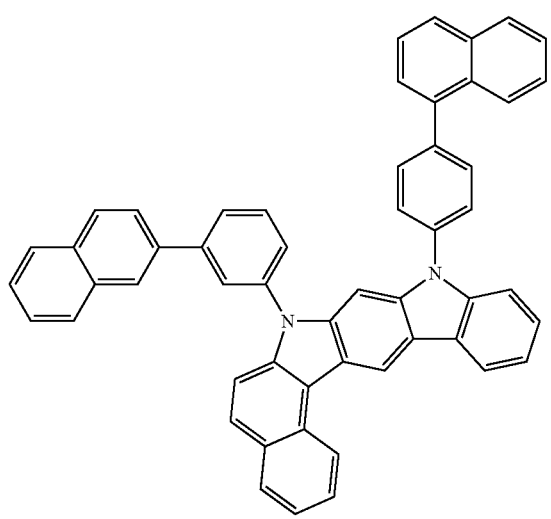
P-47
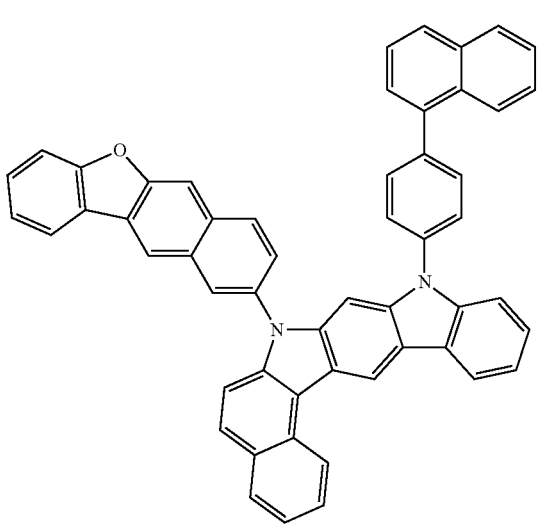
P-50
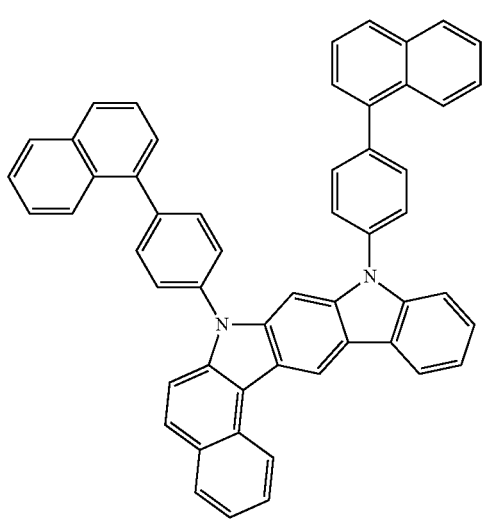
P-48
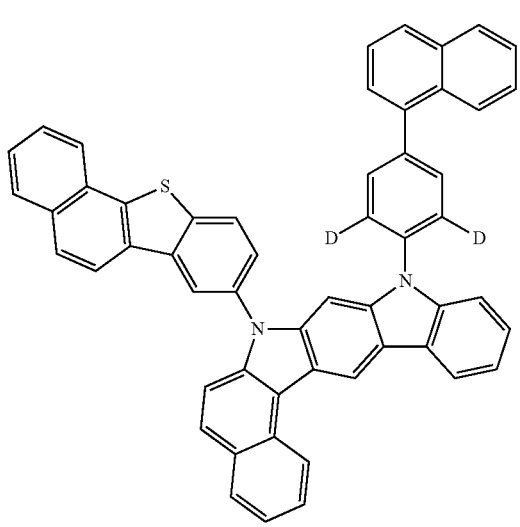
P-51
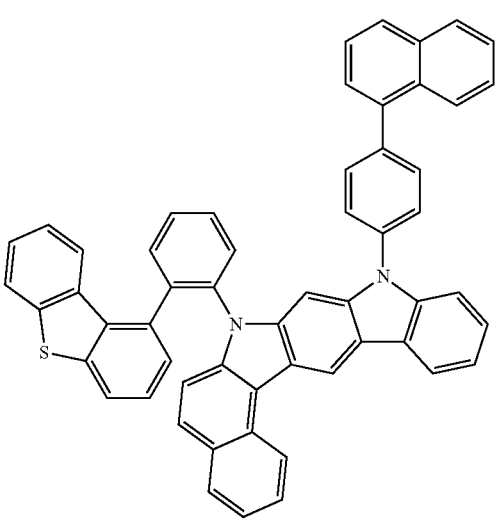

P-52
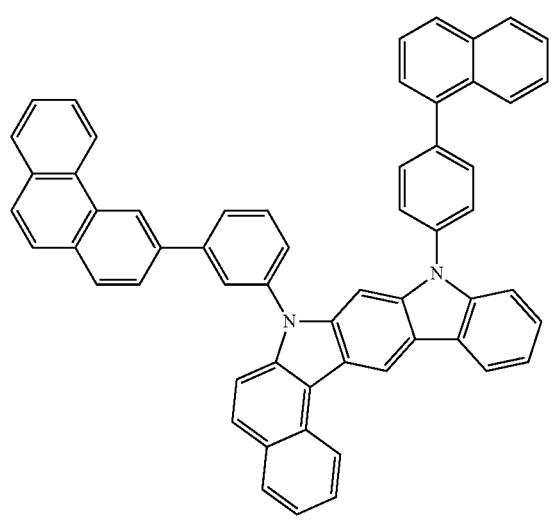
P-55
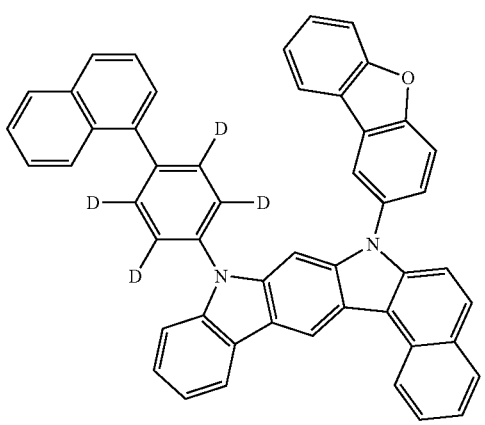
P-53
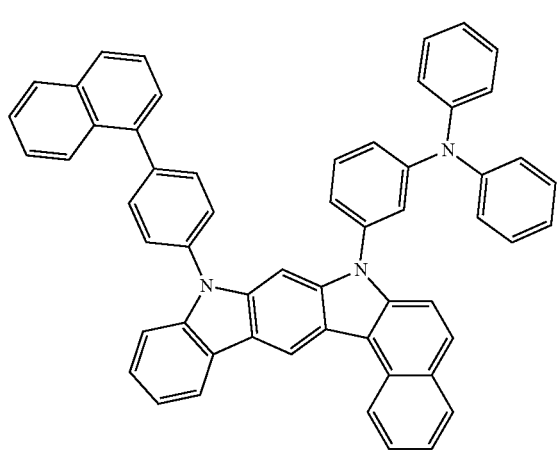
P-56
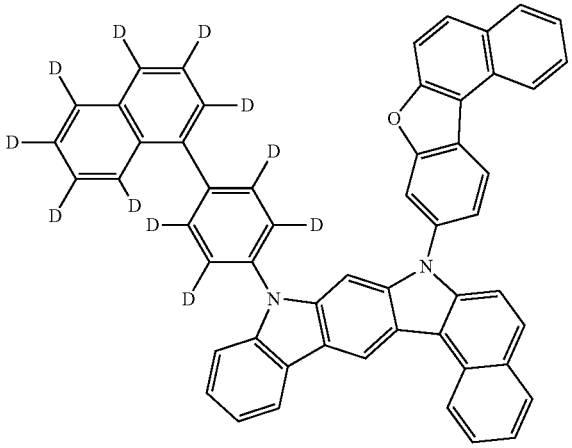
P-54
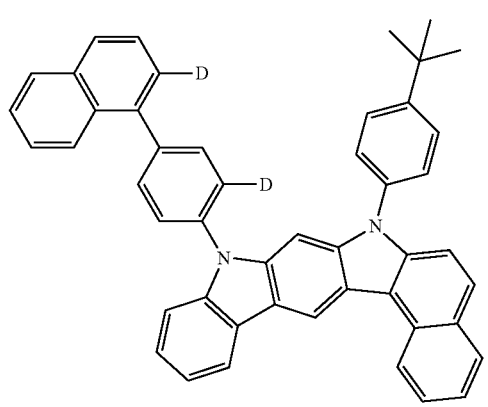
P-57
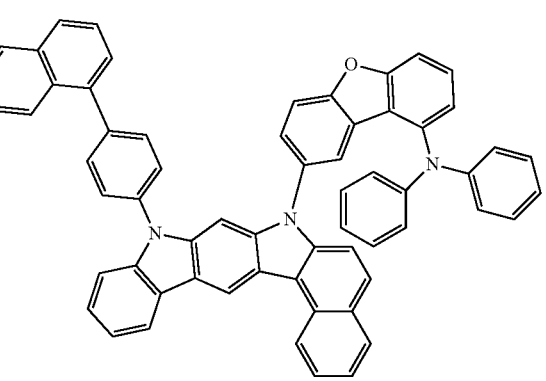

P-58

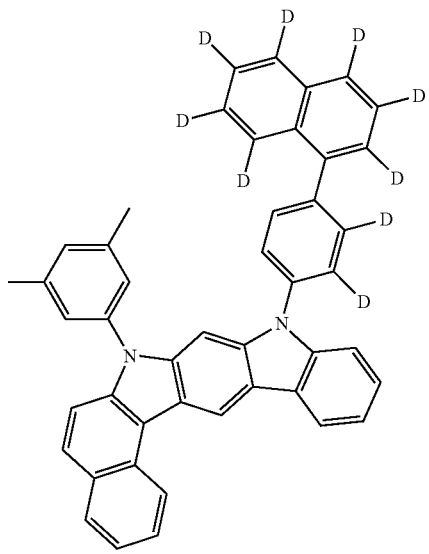

P-60

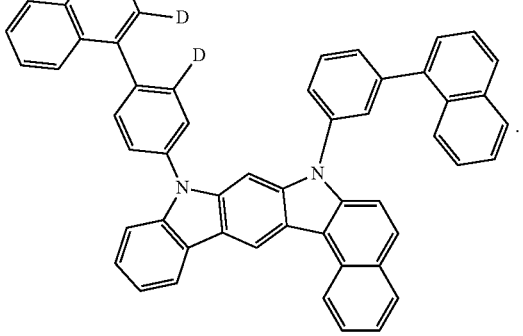

P-59

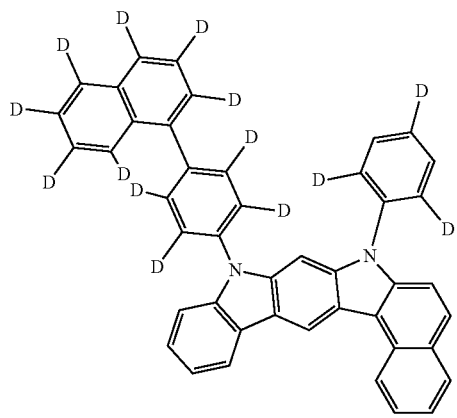

10. An organic electronic element comprising an anode, a cathode, and an organic material layer formed between the anode and the cathode, wherein the organic material layer comprises a single compound or 2 or more compounds represented by Formula (1) of claim 1.

11. The organic electronic element of claim 10, wherein the organic material layer comprises at least one of a hole injection layer, a hole transport layer, an emitting-auxiliary layer, an emitting layer, an electron transport auxiliary layer, an electron transport layer, and an electron injection layer.

12. The organic electronic element of claim 10, wherein the organic material layer is an emitting layer.

13. The organic electronic element of claim 10, further comprising a light efficiency enhancing layer formed on at least one surface of the anode and the cathode, the surface being located opposite to the organic material layer.

14. The organic electronic element of claim 10, wherein the organic material layer includes at least 2 or more stacks including a hole transport layer, an emitting layer, and an electron transport layer sequentially formed on the anode.

15. The organic electronic element of claim 14, wherein the organic material layer further comprises a charge generating layer formed between the 2 or more stacks.

16. An electronic device comprising: a display device including the organic electronic element of claim 10; and a control unit for driving the display device.

17. The organic electronic element of claim 10, wherein the organic electronic element is any one of an organic electroluminescent device (OLED), an organic solar cell, an organic photoreceptor (OPC), an organic transistor (organic TFT), and an element for monochromic or white illumination.

\* \* \* \* \*